(12) United States Patent
Yasuda et al.

(10) Patent No.: US 6,433,211 B1
(45) Date of Patent: Aug. 13, 2002

(54) PROCESS FOR PRODUCING CYANOBENZOIC ACID DERIVATIVES

(75) Inventors: Hiroshi Yasuda, Kanagawa; Haruaki Ito, Tokyo; Takashi Tani, Kanagawa; Kimitaka Ohshiro, Kanagawa; Makoto Saito, Kanagawa; Sumio Soya; Kuniomi Marumo, both of Tokyo, all of (JP)

(73) Assignee: Showa Denko Kabushiki Kaisha, Tokyo (JP)

( * ) Notice: Subject to any disclaimer, the term of this patent is extended or adjusted under 35 U.S.C. 154(b) by 0 days.

(21) Appl. No.: 09/404,362

(22) Filed: Sep. 24, 1999

Related U.S. Application Data
(60) Provisional application No. 60/104,155, filed on Oct. 14, 1998.

(30) Foreign Application Priority Data

| Sep. 24, 1998 | (JP) | 10-270213 |
| Oct. 9, 1998 | (JP) | 10-287796 |
| Oct. 14, 1998 | (JP) | 10-291963 |
| Oct. 23, 1998 | (JP) | 10-302960 |
| Oct. 23, 1998 | (JP) | 10-302961 |
| Nov. 17, 1998 | (JP) | 10-326211 |
| Nov. 18, 1998 | (JP) | 10-328171 |
| Apr. 15, 1999 | (JP) | 11-107365 |
| Apr. 21, 1999 | (JP) | 11-113621 |

(51) Int. Cl.[7] .................................................. C07C 255/00
(52) U.S. Cl. ...................................... 558/415; 558/416
(58) Field of Search ................................ 558/415, 516

(56) References Cited

U.S. PATENT DOCUMENTS 2,848,491 A * 8/1958 MacKenzie
3,962,326 A * 6/1976 Semler
4,629,700 A 12/1986 Prevatt et al.

FOREIGN PATENT DOCUMENTS

DE 28 17 505 10/1979

OTHER PUBLICATIONS

L.G. Wade, Jr. Organic Chemistry, Printice Hall p. 1009, 1995.*

Abstract, JP52039648 A, Sanpo Kagaku Kenkyusho, Mar. 28, 1977, London.

Abstract, JP2000086610 A, Showa Denko KK, Mar. 28, 2000, London.

Abstract, WO9961411 A, Showa Denko KK, Dec. 2, 1999, London.

* cited by examiner

*Primary Examiner*—Paul J. Killos
(74) *Attorney, Agent, or Firm*—Sughrue Mion, PLLC

(57) ABSTRACT

A process for producing a cyanobenzoic acid compound, a cyanobenzamide compound, an alkyl cyanobenzoate compound, and a cyanobenzoyl chloride compound, which are useful intermediates for a variety of chemicals such as pharmaceuticals, agrochemicals, liquid crystals, and monomers for functional polymers. One nitrile group of an easily available phthalonitrile compound is selectively hydrolyzed to thereby produce a cyanobenzamide compound with high selectivity and yield. The cyanobenzamide compound thus-produced is transformed under acidic conditions into a cyanobenzoic acid compound and a cyanobenzoate ester compound without the cyano group of the benzene ring being damaged.

48 Claims, No Drawings

PROCESS FOR PRODUCING CYANOBENZOIC ACID DERIVATIVES

CROSS REFERENCE TO RELATED APPLICATIONS

This application is an application filed under 35 U.S.C. §119(e)(I) of the filing date of the Provisional Application No. 60/104,155 filed Oct. 14, 1998 pursuant to 35 U.S.C. §111(b).

FIELD OF THE INVENTION

The present invention relates to a process for producing cyanobenzoic acid derivatives, and more particularly, to a process for producing a cyanobenzoic acid compound, a cyanobenzamide compound, an alkyl cyanobenzoate compound, and a cyanobenzoyl chloride compound by use of a phthalonitrile compound as a raw material.

The cyanobenzoic acid compound, cyanobenzamide compound, alkyl cyanobenzoate compound, and cyanobenzoyl chloride compound which are produced through the process according to the present invention are useful intermediates for a variety of chemicals such as pharmaceuticals, agrochemicals, liquid crystals, and monomers for functional polymers.

BACKGROUND OF THE INVENTION

Firstly, conventional processes for producing a cyanobenzamide compound will be described.

A variety of methods for selectively converting one nitrile group of a phthalonitrile compound into an amide group are known. Examples thereof include (1) hydration in the presence of an acid catalyst; (2) hydration in the presence of a base catalyst; (3) reaction with hydrogen peroxide under basic conditions; (4) reaction of a nitrile group with a carbo cation; and (5) reaction of a nitrile group with an amine. However, these methods involve problems. For example, a phthalonitrile compound must be hydrated under strong acidic conditions due to the poor reactivity of the compound. Such acidic conditions induce corrosion of the material of the reactor used, for example. JP-A-52-39648 (the term "JP-A" as used herein means an "unexamined published Japanese patent application")and *J. Gen. Chem. USSR*, 33, 631, (1963) disclose methods for selectively converting one nitrile group of a phthalonitrile compound into an amide group. The former method employs expensive sodium or potassium alkoxide, whereas the latter method discloses reaction of a terephthalonitrile compound with aqueous ammonia, the method requiring high temperature and high pressure and providing low selectivity. Thus, neither of these methods can serve as a low-cost process for producing a cyanobenzamide compound. *Collectionn Czechoslov. Chem. Commun.*, 39, 2667, (1974) discloses reaction with hydrogen peroxide under basic conditions. The reaction has poor selectivity, to thereby produce a large amount of a phthalic diamide compound, and generates a large amount of oxygen. Thus, the method is industrially unsuitable. Reaction of a nitrile group with a carbocation or reaction of a nitrile group with an amine is primarily employed for synthesis of a secondary acid amide rather than synthesis of a cyanobenzamide compound. Other processes are employed for producing a cyanobenzamide compound by use of a phthalonitrile compound as a raw material. For example, JP-A-2-108655 discloses such a process involving reaction of terephthalonitrile and acetamide in the presence of palladium bromide, and *Synthesis*, 12, 1034, (1984) discloses such a process involving reaction of terephthalonitrile and 2,2,6,6-tetramethylpiperidin-1-oxide. However, the former process has a poor yield and the latter process employs expensive materials. As described above, no known method is industrially advantageous for selectively converting one nitrile group of a phthalonitrile compound into an amide group.

Secondly, conventional processes for producing a cyanobenzoic acid compound will be described.

JP-A-64-47, *Dokl. Akad. Nauk. SSSR*, 312, 5, 1129, (1990), and *J. Organomet. Chem.*, 358, 1–3, 563, (1988) disclose processes involving reaction of a halobenzonitrile, such as chlorobenzonitrile, with carbon monoxide in the presence of a catalyst. SU 1,467,053 and *Azerv. Khim. Zh.*, 1, 26, (1983) disclose processes involving oxidation of the methyl group of tolunitrile. U.S. Pat. No. 4,213,917 and WO 9009975 disclose processes involving oxidation of the aldehyde group of cyanobenzaldehyde. JP-A-50-71643 and JP-A-50-83346 disclose processes involving disproportionation between a nitrile and a carboxylic acid. These processes also involve problems. For example, raw materials are difficult to obtain or expensive, and severe conditions are required. Thus, these methods are not industrially advantageous and are insufficient as low-cost methods.

Among cyanobenzoic acid compounds, p-cyanobenzoic acid is synthesized in a classic manner; i.e., Sandmeyer's reaction in which p-aminobenzoic acid is diazotized and the diazo species is reacted with copper cyanide (Lucas et al., *J. Am. Chem. Soc.*, 51 (1929) 2718). Alternatively, processes for the synthesis involving oxidation of tolunitrile with a strong oxidizing agent such as chromic acid or permanganic acid (Levine et al., *J. Org. Chem.*, 24 (1959) 115; and Kattwinkel et al., *Chem. Ber.*, 37 (1904) 3226). These processes also involve problems. For example, Sandmeyer's reaction requires toxic copper cyanide; particularly, isolation and purification of p-cyanobenzoic acid under acidic conditions is difficult and dangerous due to generation of free hydrogen cyanide. Use of an oxidizing agent such as chromic acid or permanganic acid entails producing a toxic heavy metal waste as a by-product, which causes production of a large amount of toxic wastewater and thereby involves an environmental problem.

JP-A-61-85194 discloses that one nitrile group of terephthalonitrile is biologically hydrolyzed with an enzyme such as mononitrilase, to thereby synthesize p-cyanobenzoic acid. However, selectivity of hydrolysis of one nitrile group is poor, and hydrolysis must be carried out under low-concentration conditions, to thereby result in low productivity. In addition, by-products such as terephthalamic acid, terephthalamide, and terephthalic acid are inevitably produced along with the target p-cyanobenzoic acid.

Arkhipova et al., *J. Gen. Chem. USSR*, 33 (1963) 631 disclose a process involving hydrolysis of one nitrile group of terephthalonitrile with pressurized aqueous ammonia. It is reported that one nitrile group of terephthalonitrile is hydrated to form p-cyanobenzamide, and the amide group thereof is further hydrolyzed to form p-cyanobenzoic acid. However, the above hydrolysis requires high temperature and pressure and is not preferred, in consideration of safety.

As described above, conventionally known techniques for producing p-cyanobenzoic acid disadvantageously involve problems such as poor operational safety, formation of by-products, and difficulty in attaining production of high-purity compounds.

Thirdly, conventional processes for producing an alkyl cyanobenzoate compound will be described.

JP-A-58-113145 discloses a process involving reaction of carbon monoxide and an alcohol in the presence of chlorobenzonitrile serving as a catalyst. *Bull. Chem. Soc. Jpn.*, 61, 6, 1985 (1988) and *J. Org. Chem.*, 51, 24, 4714, (1986) disclose a process for producing methyl aminobenzoate involving Sandmeyer's reaction and a diazonium salt. JP-B-41-18818 (the term "JP-B" as used herein means an "examined Japanese patent publication") discloses such a process involving disproportionation between a nitrile and an ester. The process employing carbon monoxide and the process involving Sandmeyer's reaction involve a raw material availability problem. The above disproportionation disadvantageously requires severe reaction conditions. Thus, no industrially advantageous and low-cost process for producing an alkyl cyanobenzoate compound has been known.

Fourthly, conventional processes for producing a cyanobenzoyl chloride compound will be described.

p-Cyanobenzoyl chloride is synthesized through reaction of p-cyanobenzoic acid with a chlorinating agent. Examples of chlorinating agents include thionyl chloride (JP-B-1-31501, Johan Kamphuis, et al., *J. Chem. Soc. Perkin Trans.*, 2 (1987) 907), oxalyl chloride (Robert J. Weikert, et al., *J. Med. Chem.*, 34 (1991) 1630), and phosphorus pentachloride (Raffaello Fusco, et al., *Ann. Chim. (Rome)*, 42 (1952) 94). As an alternative to chlorination to produce an acid chloride, JP-A-63-313761 discloses a process involving reaction of 4-trichloromethylbenzamide in the presence of ferric chloride as a catalyst, and JP-A-52-39649 discloses a process involving reaction of a terephthalamate salt and phosphorus oxychloride.

Conventional processes for chlorinating a p-cyanobenzoic acid compound to produce the corresponding acid chloride also involve problems. When thionyl chloride is used, sulfur dioxide which is generated must be separated for detoxification, which is not economical. When oxalyl chloride is used, highly toxic carbon monoxide produced therefrom must be separated for detoxification, which is not economical. When phosphorus pentachloride is used, a compound produced from the reaction must be removed in order to prevent eutrophication of lakes, ponds, and rivers, and such an excess step for the sake of environmental safety disturbs practical application of phosphorous pentachloride. Terephthalamate salt and 4-trichloromethylbenzamide, serving as raw materials for a process involving reaction therebetween, are expensive and are not easily available, to thereby make the process economically disadvantageous.

As described above, conventional processes for producing a p-cyanobenzoyl chloride compound involve problems such as dangerous steps for separation and removal of by-products, and poor availability of raw materials.

SUMMARY OF THE INVENTION

In view of the foregoing, an object of the present invention is to provide a process for producing a cyanobenzamide compound with high selectivity and yield from a phthalonitrile compound which is a raw material that is easily available on an industrial scale.

Another object of the present invention is to provide a process for producing a cyanobenzoic acid compound and an alkyl cyanobenzoate compound with high selectivity and yield from the thus-produced cyanobenzamide compound serving as a raw material.

Still another object of the invention is to provide a process for producing a cyanobenzoic acid compound with high selectivity and yield from an alkyl cyanobenzoate compound serving as a raw material.

Yet another object of the invention is to provide a process for producing a cyanobenzoyl chloride compound with high selectivity and yield in an industrially advantageous manner.

The present inventors have conducted earnest studies, and they are able to satisfy the above objects.

Accordingly, a first aspect of the present invention provides a process for producing a cyanobenzoic acid compound, which comprises transforming a cyanobenzamide compound into a cyanobenzoic acid compound under an acidic condition.

Preferably, the cyanobenzamide compound is reacted with hypohalogenous acid and/or another halogenous acid under an acidic condition to thereby exclusively transform the amide group into a carboxyl group.

Preferably, a process for producing a cyanobenzoic acid compound comprises the steps of selectively hydrating one nitrite group of a phthalonitrile compound in an aliphatic alcohol serving as a solvent in the presence of a base to thereby produce a cyanobenzamide compound, and reacting the cyanobenzamide compound with a hypohalogenenous acid and/or a halogenous acid under an acidic condition to thereby exclusively transform the amide group into a carboxyl group.

Preferably, the cyanobenzamide compound is reacted with hypohalogenenous acid and/or halogenous acid under an acidic condition, the reaction mixture having a pH of 7 or less.

Preferably, the cyanobenzamide compound is reacted with nitrous acid under an acidic condition.

Additionally, nitrous acid is generated through reaction of a nitrite salt with an acid.

Further, the above reaction is carried out in a strongly acidic aqueous solvent at 5–60° C.

Alternatively, the reaction is preferably carried out in a substantially water-free and acidic organic solvent in the temperature range of −10° C. to 100° C.

Preferably, 1 mol of a cyanobenzamide compound is reacted with a nitrite salt in an amount at least equimol to mol.

Alternatively, in the first aspect of the invention, the cyanobenzamide compound is preferably reacted with a nitrosonium salt compound under an acidic condition.

Preferably, the reaction is carried out in a substantially water-free organic solvent.

Alternatively, in the first aspect of the invention, the cyanobenzamide compound is preferably reacted with a nitrogen oxide.

Preferably, the reaction is carried out in an organic solvent.

Preferably, the organic solvent is a polar organic solvent.

Preferably, the polar organic solvent is a mixture of a carboxylic acid and a carboxylic anhydride.

Preferably, the above reaction is carried out in the presence of a base.

Preferably, the base is a carboxylate salt.

Preferably, the above reaction is carried out in an aqueous acidic solution.

Preferably, the cyanobenzamide compound is a compound represented by the following formula:

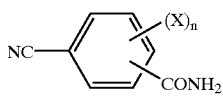

(1)

wherein each of —CONH$_2$ and —X represents a substituent on the benzene ring; the —CONH$_2$ group is bonded at the m- or the p-position with respect to the CN group; X represents a chlorine atom or a fluorine atom; n is an integer between 0 and 4 inclusive; and when n is 2 or more the plurality of X's may be identical to or different from one another, and the cyanobenzoic acid compound is a compound represented by the following formula:

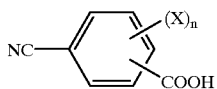

(2)

wherein each of —COOH and —X represents a substituent on the benzene ring; the —COOH group is bonded at the m- or the p-position with respect to the CN group; X represents a chlorine atom or a fluorine atom; n is an integer between 0 and 4 inclusive; and when n is 2 or more the plurality of X's may be identical to or different from one another.

Preferably, the cyanobenzamide compound represented by formula (1) is m-cyanobenzamide or p-cyanobenzamide, and thee cyanobenzoic acid compound represented by formula (2) is m-cyanobenzoic acid or p-cyanobenzoic acid.

In a second aspect of the present invention, there is provided a process for producing a cyanobenzamide compound, which comprises selectively hydrating one nitrile group of a phthalonitrile compound in an aliphatic alcohol serving as a solvent, in the presence of a base.

Preferably, there is provided the process for producing a cyanobenzamide compound described above, wherein the phthalonitrile compound is a compound represented by the following formula:

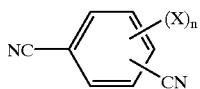

(3)

wherein one nitrile group is bonded at the m- or the p-position with respect to the other nitrile group; X represents a chlorine atom or a fluorine atom; n is an integer between 0 and 4 inclusive; and when n is 2 or more the plurality of X's may be identical to or different from one another, and the cyanobenzamide compound is a compound represented by the following formula:

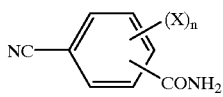

(1)

wherein X and n have the same definitions as described above, and the —CONH$_2$ group is bonded at the m- or the p-position with respect to the CN group.

More preferably, the phthalonitrile compound represented by formula (3) is isophthalonitrile or terephthalonitrile, and the cyanobenzamide compound represented by formula (1) is m- or p-cyanobenzamide.

Preferably, the base comprises one or more species selected from the group consisting of an alkali metal hydroxide, an alkali metal carbonate, an alkali metal phosphate, an alkaline earth metal hydroxide, and an amine.

Preferably, the base is used in an amount of 0.01–1 mol based on 1 mol of phthalonitrile compound.

Preferably, the aliphatic alcohol is a tertiary alcohol.

Preferably, hydration is carried out within the temperature range of 0° C. to the reflux temperature of the employed solvent.

More preferably, during hydration water is added in an amount of 0.2–10 mol based on 1 mol of the phthalonitrile compound.

In a third aspect of the present invention, there is provided a process for producing an alkyl cyanobenzoate compound from a phthalonitrile compound, which comprises the steps of reacting a phthalonitrile compound and an aliphatic alcohol in the presence of an acid to thereby transform exclusively one nitrile group into an alkylimino ether group; and selectively reacting the formed alkylimino ether group with water to thereby transform the ether group into an alkyl ester group.

Preferably, the phthalonitrile compound is a compound represented by the following formula:

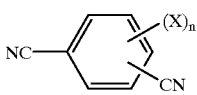

(3)

wherein —CN, n, and X have the same definitions as described above, the aliphatic alcohol in the first step is represented by the following formula

ROH     (4)

wherein R represents a C$_1$–C$_5$ alkyl group, and the alkyl cyanobenzoate compound is a compound represented by the following formula:

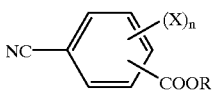

(5)

wherein X, n, and R have the same definitions as described above and the —COOR group is bonded at the m- or the p-position with respect to the nitrile group.

More preferably, the phthalonitrile compound represented by formula (3) is isophthalonitrile or terephthalonitrile, and the alkyl cyanobenzoate compound represented by formula (5) is alkyl m- or p-cyanobenzoate.

Preferably, the aliphatic alcohol represented by formula (4) is methanol or ethanol.

Preferably, the unreacted phthalonitrile compound is collected and reused as a raw material.

In a fourth aspect of the present invention, there is provided a process for producing an alkyl cyanobenzoate compound, which comprises the step of reacting a cyanobenzamide compound and an aliphatic alcohol in the presence of an acid to thereby transform exclusively the amide group into an alkyl ester group.

Preferably, the cyanobenzamide compound is a compound presented by the following formula:

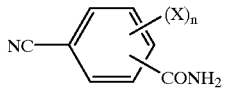

(1)

wherein each of —CONH$_2$ and —X represents a substituent of the benzene ring; the —CONH$_2$ group is bonded at the m- or the p-position with respect to the CN group; X represents a chlorine atom or a fluorine atom; n is an integer between 0 and 4 inclusive; and when n is 2 or more the plurality of X's may be identical to or different from one another, the aliphatic alcohol is represented by the following formula:

ROH    (4)

wherein R represents a C$_1$–C$_5$ alkyl group, and the alkyl cyanobenzoate compound is represented by the following formula:

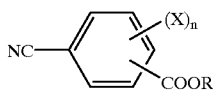

(5)

wherein X, n, and R have the same definitions as described above and the —COOR group is bonded at the m- or the p-position with respect to the nitrile group.

Preferably, the cyanobenzamide compound represented by formula (1) is m- or p-cyanobenzamide, and the alkyl cyanobenzoate compound represented by formula (5) is alkyl m- or p-cyanobenzoate.

Preferably, the aliphatic alcohol represented by formula (4) is methanol or ethanol.

In a fifth aspect of the present invention, there is provided a process for producing a cyanobenzoic acid compound, which comprises the step of oxidizing a cyanobenzylamine compound.

Preferably, the cyanobenzylamine compound is oxidized in the presence of a ruthenium oxide compound or an iron oxide compound.

More preferably, the above-described oxidation step is carried out by use of an oxidizing agent other than a ruthenium oxide compound or an iron oxide compound, in the presence of the ruthenium oxide compound or the iron oxide compound.

Preferably, the oxidizing agent is a hypohalogeous acid compound or a persulfate salt compound.

Preferably, the above-described oxidation step is carried out in water or water containing an aprotic polar solvent.

Preferably, the above-described oxidation step is carried out at a pH of 7.5–12.

Preferably, the cyanobenzylamine compound is a compound represented by the following formula:

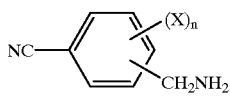

(6)

wherein each of —CH$_2$NH$_2$ and —X represents a substituent of the benzene ring; the —CH$_2$NH$_2$ group is bonded at the m- or the p-position with respect to the CN group; X represents a chlorine atom or a fluorine atom; n is an integer between 0 and 4 inclusive; and when n is 2 or more the plurality of X's may be identical to or different from one another, and the cyanobenzoic acid compound is a compound represented by the following formula:

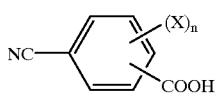

(2)

wherein —COOH, —X, and —CN have the same definitions as described above.

Preferably, the cyanobenzylamine compound represented by formula (6) is m- or p-cyanobenzylmaine, and the cyanobenzoic acid compound represented by formula (2) is m- or p-cyanobenzoic acid.

In a sixth aspect of the present invention, there is provided a process for producing a cyanobenzoic acid compound represented by the following formula:

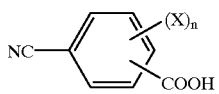

(2)

wherein —COOH, —X, and —CN have the same definitions as described above, which process comprises the steps of exclusively hydrolyzing the alkyl ester group of an alkyl cyanobenzoate compound represented by the following formula:

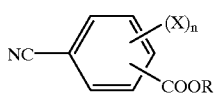

(5)

wherein X, n, and R have the same definitions as described above and the —COOR group is bonded at the m- or the p-position with respect to the nitrile group, in the presence of a base, to thereby synthesize a salt of the corresponding cyanobenzoic acid compound, and adding an acid in order to release the corresponding free form of the cyanobenzoic acid compound.

Preferably, the alkyl cyanobenzoate compound represented by formula (5) is alkyl m-cyanobenzoate or alkyl p-cyanobenzoate, and the cyanobenzoic acid compound represented by formula (2) is m-cyanobezoic acid or p-cyanobenzoic acid.

Preferably, in the first step, hydrolysis is carried out in the presence of an alkali metal hydroxide or carbonate.

Preferably, in the first step, hydrolysis is carried out at a pH of 8–12.

Preferably, the alkyl cyanobenzoate compound represented by formula (5) is methyl cyanobenzoate or ethyl cyanobenzoate.

In a seventh aspect of the present invention, there is provided a process for producing a cyanobenzoyl chloride compound represented by the following formula:

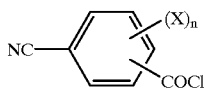

(7)

wherein each of —COCl and —X represents a substituent of the benzene ring; the —COCl group is bonded at the m- or the p-position with respect to the CN group; X represents a chlorine atom or a fluorine atom; n is an integer between 0 and 4 inclusive; and when n is 2 or more the plurality of X's may be identical to or different from one another, which process comprises reacting a cyanobenzoic acid compound represented by the following formula:

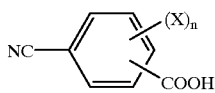

(2)

wherein —COOH, —X, and —CN have the same definitions as described above, with phosgene or a precursor thereof.

Preferably, the above-described reaction is carried out in the presence of a cyanobenzoyl chloride compound corresponding to the cyanobenzoic acid compound.

Preferably, the above-described reaction is carried out in the presence of a tertiary amide compound or a tertiary amine compound.

Preferably, the cyanobenzoic acid compound represented by formula (2) is m- or p-cyanobenzoic acid, and the cyanobenzoyl chloride compound represented by formula (7) is m- or p-cyanobenzoyl chloride.

DETAILED DESCRIPTION OF PREFERRED EMBODIMENTS (A) Process for Producing a Cyanobenzoic Acid Compound from a Cyanobenzamide Compound as a Raw Material The process comprises exclusively transforming the amide group of an cyanobenzamide compound into a carboxylic group under an acidic condition, to thereby produce a cyanobenzoic acid compound.

Specifically, the process is classified into one of four types in accordance with the reactant used, i.e., (i) a process employing hypohalogenous acid and/or halogenous acid; (ii) a process employing a nitrate salt; (iii) a process employing a nitrosonium salt; and (iv) a process employing a nitrogen oxide. Each process described in detail below.

(i) Process Employing Hypohalogenous Acid and/or Halogenous Acid

In this process, a cyanobenzamide compound is reacted with hypohalogenous acid and/or halogenous in an alcohol while an acid is added so as to maintain the reaction mixture acidic, to thereby exclusively transform the amide group into a carboxyl group. Alternatively, the process comprises the steps of adding a base and water in suitable amounts so as to transform one nitrile group of a phthalonitrile compound to an amide group in an alcohol, to thereby produce a cyanobenzamide compound (first reaction) and reacting the cyanobenzamide compound with hypohalogenenous and/or halogenous acid while an acid is added so as to maintain the reaction mixture acidic, to thereby exclusively transform the amide group into a carboxyl group (second reaction).

Examples of unsubstituted cyanobenzamide compounds which can be used in the present invention include p-cyanobenzamide and m-cyanobenzamide. These cyanobenzamides may be synthesized through known methods for hydrating one nitrile group of terephthalonitrile or isophthalonitrile described in Berther et al., *Chem. Ber.,* 92 (1959) 2116, or through one of the processes of the present invention as described below.

Examples of halo-substituted cyanobenzamide compounds include chlorinated cyanobenzamide compounds such as 4-cyano-2,3,5,6-tetrachlorobenzamide and 3-cyano-2,4,5,6-tetrachlorobenzamide, and fluorinated cyanobenzamide compounds such as 4-cyano-2,3,5,6-tetrafluorobenzamide and 3-cyano-2,4,5,6-tetrafluorobenzamide. These halo-substituted cyanobenzamide compounds may be synthesized through the above-described method, or through one of the processes of the present invention as described below, in which one nitrile group of a chlorinated terephthalonitrile compound such as tetrachloroterephthalonitrile; a chlorinated isophthalonitrile compound such as tetrachloroisophthalonitrile; a fluorinated terephthalonitrile compound such as tetrafluoroterephthalonitrile; and a fluorinated isophthalonitrile compound such as tetrafluoroisophthalonitrile is hydrated, the chlorinated species being formed through chlorination and the fluorinated species being obtained through fluorination of the chlorinated species.

Substituted or unsubstituted phthalonitrile may be used as the phthalonitrile compound employed in the present invention. Examples of preferable unsubstituted phthalonitriles include isophthalonitrile and terephthalonitrile. Examples of substituted phthalonitriles include phthalonitrile which has 1 to 4 substituents from among a halogen atom, an alkyl group, an aryl group, an aralkyl group, an alkoxy group, an aryloxy group, and an aralkyloxy group. When phthalonitrile has two or more substituents, these may be identical or different from one another.

A halo-substituted phthalonitrile is herein described. As described herein, a chlorinated phthalonitrile compound such as tetrachloroisophthalonitrile or tetrachloroterephthalonitrile can be produced through chlorination of isophthalonitrile or terephthalonitrile, respectively. Similar fluorinated species can be produced through fluorination of the corresponding chlorinated species.

Examples of alcohols which can be used in the first reaction include methanol, ethanol, n-propanol, n-butanol, n-pentanol, isopropanol, isobutanol, sec-butanol, tertbutanol, isoamyl alcohol, 2-methylbutanol-(1), neopentyl alcohol, ethylene glycol, and propylene glycol. Of these, tert-butanol and ethanol are preferred.

Although the temperature of the first reaction is not particularly limited, the temperature is preferably 0–100° C. The reaction time must be appropriately adjusted in accordance with the type of the alcohol or the phthalonitrile compound. Preferably, the reaction time is adjusted such that the conversion of the phthalonitrile compound reaches 20–80% and the yield of phthalic diamide as an impurity is 1% or less. When the reaction time is excessively long, phthalic diamide as an impurity is transformed into terephthalic acid in the second reaction, to thereby reduce the purity of the finally obtained cyanobenzoic acid; whereas the reaction time is short, the yield of the target product decreases.

Unreacted phthalonitrile compound has very poor solubility in an aqueous alcohol solution, whereas a cyanobenzoic acid compound is dissolved into a reaction mixture through formation of salt thereof when the pH is elevated. By use of the difference in solubility, the unreacted phthalonitrile compound can be easily removed through filtration after completion of the second reaction, and can be used again.

Examples of bases which can be used in the first reaction include alkali metal hydroxides such as sodium hydroxide and potassium hydroxide; alkali metal carbonates such as sodium carbonate; alkali metal phosphates such as trisodium phosphate; alkaline earth metal hydroxides such as calcium hydroxide; and ammonia. Of these, sodium hydroxide and potassium hydroxide are preferred.

These base components may be used alone or as a combination of two or more species, and they may be added to the reaction mixture in the form of solid or in the form of an aqueous solution.

The base is preferably added in a mol ratio based on phthalonitrile of 0.01–1. When the mol ratio is less than 0.01, reactivity disadvantageously decreases; whereas when the ratio is in excess of 1, two nitrile groups of a phthalonitrile compound are reacted to form phthalic diamide as a disadvantageous by-product.

In the first reaction, water is added in an amount of 0.1–8 mol based on 1 mol of a phthalonitrile compound, preferably 0.2–4 mol.

No particular limitation is imposed on the manner of addition of base and water, and the base and water can be added simultaneously, or either can be added in advance of the other. Base or water may be added at one time or gradually.

After completion of the first reaction, the reaction mixture is preferably neutralized. When the reaction mixture is allowed to stand for a long period of time without neutralization, problems occur, in that the yield of the target compound decreases and terephthalic diamide and isophthalic diamide serving as impurities increase.

The reaction mixture of the first reaction may be directly used in the second reaction.

The reaction temperature of the second reaction falls within the range of −20° C. to 100° C., preferably −10° C. to 80° C., more preferably 0C to 60° C. A very low temperature requires addition of a source of hypohalogenous acid and/or halogenous acid in a large amount so as to overcome poor reactivity, whereas a high temperature results in conversion of the nitrile group to the amide group and, further to the carboxyl group, to thereby reduce the yield and purity of the target compound.

In the second reaction, the source of hypohalogenous acid and/or halogenous acid is added in an amount of 0.1–12.5 mol based on 1 mol of the cyanobenzamide compound, preferably 1.2–10 mol.

The reaction time of the second reaction is 10 minutes to 48 hours, preferably 1–24 hours. A short reaction time disadvantageously decreases the conversion of the cyanobenzamide compound, whereas a long reaction time disadvantageously decreases the yield and productivity of the target compound.

No particular limitation is imposed on the source of hypohalogenous acid and/or halogenous acid, and a commercially available source may be used. Examples thereof include sodium hypochlorite, potassium hypochlorite, calcium hypochlorite, barium hypochlorite, sodium hypobromite, potassium hypobromite, calcium hypobromite, sodium chlorite, potassium chlorite, calcium chlorite, barium chlorite, sodium bromite, potassium bromite, calcium bromite, and barium bromite. Of these, sodium hypochlorite is preferred.

The source of hypohalogenous acid and/or halogenous acid is used in an amount of 0.1–10 mol based on 1 mol of the phthalonitrile compound used in the first reaction, preferably 1–8 mol. Small amounts decrease the conversion rate of the cyanobenzamide compound, to thereby decrease the yield of the target compound. In contrast, large amounts do not impair the reaction, but cause a large amount of a salt to intermingle with the product to thereby disadvantageously reduce the purity thereof.

No particular limitation is imposed on the pH of the reaction mixture, and during reaction the pH is preferably adjusted to 7 or lower through addition of an acid, more preferably 4–6.5. An excessively high pH results in poor reactivity; i.e., a cyanobenzamide compound is converted to a reaction intermediate, but the intermediate still remains and does not react further, to thereby fail to form a cyanobenzoic acid compound. A very low pH causes precipitation of a cyanobenzoic acid compound, to disadvantageously interrupt stirring.

When a phthalonitrile compound is used as a starting material, the pH of the reaction mixture is adjusted to 4 or higher, preferably 7–12, so as to separate a formed cyanobenzoic acid compound from the unreacted phthalonitrile compound remaining after completion of the second reaction. Through such adjustment of the pH, a salt of the cyanobenzoic acid compound is dissolved in the reaction mixture, and the insoluble phthalonitrile compound can be isolated by means of filtration. When the pH of the reaction mixture is excessively high, the nitrite group of the cyanobenzoic acid compound is hydrolyzed to thereby decrease the yield, whereas when the pH is low, the cyanobenzoic acid is disadvantageously precipitated in the form of a free acid rather than in the form of a salt. The thus-isolated crystals of the phthalonitrile compound can be recycled.

After separation of the phthalonitrile compound through filtration, the pH of the filtrate containing a salt of the cyanobenzoic acid compound is adjusted to 4 or lower, preferably 3.5 or lower, to thereby transform the salt into the corresponding acid. The obtained cyanobenzoic acid compound may be optionally recrystallized from an aqueous alcohol solution, to thereby produce high-purity crystals of the cyanobenzoic acid compound.

(ii) Process Employing a Nitrite Salt

In this process, a cyanobenzamide compound serving as a raw material, a nitrite salt, and a solvent such as an aqueous solvent or an organic solvent are placed in a reactor, and the mixture is allowed to react at a predetermined temperature for a predetermined period of time under acidic conditions with stirring. Feeding of the above materials and the reaction may be carried out under pressurized conditions or under atmospheric pressure.

The reaction mechanism of the process are next described with reference to reaction of p-cyanobenzamide for production of p-cyanobenzoic acid.

The reaction is assumed to proceed according to the following mechanism: reaction between a nitrite salt (MNO$_2$) and a protonic acid (HX) produces nitrous acid [Reaction formula (1)], and the amide group of p-cyanobenzamide reacts with nitrous acid, to thereby form p-cyanobenzoic acid (Reaction formula (2)).

$$MNO_2 + HX \rightarrow HONO + RX \quad (1)$$

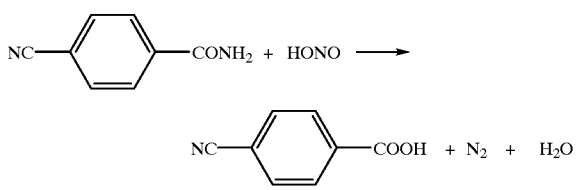

(2)

The cyanobenzamide compound employed process (i) can also be used in process (ii).

Examples of nitrite salts which can be used in the process include sodium nitrite and potassium nitrite. The nitrite salt is preferably used in an amount of 1–10 mol based on 1 mol of the cyanobenzamide compound.

The reaction is carried out under acidic conditions, preferably under strongly acidic conditions. An organic or inorganic protonic acid is employed. Examples of inorganic acids include sulfuric acid, nitric acid, hydrochloric acid, and phosphoric acid. Of these, sulfuric acid is particularly preferred, in that it also serves as a solvent.

Examples of organic acids include carboxylic acids such as acetic acid, propionic acid, and trifluoroacetic acid; and sulfonic acids such as methanesulfonic the acid and trifluoromethanesulfonic acid. Of these, a carboxylic acid having a low boiling point is particularly preferred in that it also serves as a solvent.

The amount of acid used in the process is theoretically equimol to that of the nitrite salt. However, in practice, the reaction requires an excess amount of a protonic acid other than nitrous acid present in the reaction system. When sodium nitrite is used as a nitrite salt and acid added to the reaction system is an acid weaker than nitrous acid; e.g., acetic acid, the acid must be added in a considerably large amount, equivalent to the amount of a solvent. When the acid is much stronger than nitrous acid, the acid is added in an amount of approximately 1.5 equivalents in view of the rate of reaction. When the acid serves as a solvent, concentrated sulfuric acid having a concentration of 70 wt. % or more is particularly preferably used in a volume equivalent to that of the employed solvent.

A variety of solvents can be employed in the process. For example, there may be employed water; an aqueous solvent such as a water-containing organic solvent; or a water-free organic solvent.

When the solvent is water, the reaction is carried out in the presence of an inorganic protonic acid. When the solvent is a water-containing organic solvent, the reaction is carried out in the presence of an inorganic acid or an organic acid. Typically, an organic solvent which can be homogeneously mixed with water is employed as such a solvent system. Examples of the hydrated organic solvent include ethers such as dioxane and diglyme; alcohols such as methanol and ethanol; nitrites such as acetonitrile; and carboxylic acids such as acetic acid and propionic acid.

When a substantially water-free organic solvent is used, the reaction is carried out in the presence of an inorganic acid containing no water, such as hydrochloric acid gas or an organic acid. In this case, strongly acidic conditions are not required. Examples of such organic solvents include polar amides such as formamide and dimethyformamide; sulfur-containing compounds such as dimethyl sulfoxide and sulfolane; imidazolidones such as 1,3-dimethyl-2-imidazolidione; ethers such as dioxane, 1,2-dimethoxyethane, and diglyme; halohydrocarbons such as dichloromethane, chloroform, and 1,2-dichloroethane; alcohols such as methanol and ethanol; aromatic hydrocarbons such as benzene and toluene; acid anhydrides such as acetic anhydride and propionic anhydride; and carboxylic acids such as acetic acid, trifluoroacetic acid, and propionic acid. These organic solvents may be used alone or as a combination of two or more species.

In the process, the solvent is preferably used in an amount by weight of 5–100 times that of the cyanobenzamide compound.

The reaction temperature in the case where water or a water-containing organic solvent is used differs from that in the case where a substantially water-free organic solvent is used.

When water or a water-containing organic solvent is used, the reaction temperature depends on the type and concentration of the acid. Very low reaction temperatures decrease the solubility of a cyanobenzamide compound serving as a raw material, to thereby reduce the rate of reaction; whereas excessively high reaction temperatures result in hydration and hydrolyzation of the nitrile group of the cyanobenzamide compound serving as a raw material and the nitrile group of the produced cyanobenzoic acid compound, to thereby lower the yield of the target compound. Therefore, the reaction temperature is preferably 5–60° C., more preferably 10–30° C.

In contrast, when a substantially water-free organic solvent is used, the nitrile group is very insensitive to a protonic acid and difficult to decompose. Thus, the reaction can be carried out under strongly acidic conditions by use of a strong acid such as trifluoromethanesulfonic acid while side reactions are suppressed. Therefore, the reaction temperature preferably falls within the range of −10° C. to 100° C., more preferably within the range of 0° C. to 80° C.

The reaction time is preferably 10 minutes to 10 hours, depending on the composition of the solvent.

After the reaction is completed, the formed cyanobenzoic acid compound is isolated and purified. When the reaction mixture is a strongly acidic aqueous solution, the formed cyanobenzoic acid compound is precipitated due to considerably poor solubility to water. Thus, the precipitate is separated through filtration, washed with water, and dried, to thereby produce a cyanobenzoic acid compound having a purity corresponding to that of the starting cyanobenzamide compound.

When an organic solvent is used, the cyanobenzoic acid compound formed is precipitated or still remains dissolved in the solvent, depending on the type of solvent employed. When the cyanobenzoic acid compound is precipitated, isolation and purification can be completed simply through the sequential steps of filtration, washing with water, and drying. When the formed cyanobenzoic acid compound is dissolved, the residual solvent is removed by distillation under vacuum, and water is added to the resultant residue so as to precipitate the cyanobenzoic acid compound, which is further subjected to filtration, washing with water, and drying. In this case, the cyanobenzoic acid compound produced also has a purity corresponding to that of the starting cyanobenzamide compound.

(iii) Process Employing a Nitrosonium Salt

In this process, a cyanobenzamide compound and a nitrosonium salt compound are added to an organic solvent, and the mixture is allowed to react with stirring at a predetermined temperature for a predetermined period of time.

Although the manner of feeding the above materials and the reaction is not particularly limited, feeding may typically be carried out under atmospheric pressure.

The cyanobenzamide compound employed in process (i) can also be used in process (iii).

The cyanobenzamide compound is reacted with a nitrosonium salt compound, which has a formula $NO^+X^{31}$, wherein X represents a monovalent cation, and is generally an ionic crystalline solid. Examples of nitrosonium salt compounds include $NOClO_4$, $NOSO_3F$, $NOHSO_4$, $NOSCN$, $NOBF_4$, $NOPF_4$, $NOAsF_4$, $NOSbF_4$, $NOFeCl_4$, and $NOMoF_6$. Of these, $NOHSO_4$ and $NOBF_4$ are preferred.

The nitrosonium salt compound may be synthesized separately in advance or prepared in the reaction system during use.

The nitrosonium salt compound is preferably used in an amount of 1–5 mol based on 1 mol of the cyanobenzamide compound.

The reaction is preferably carried out in a substantially water-free organic solvent. Examples of such organic solvents include polar amides such as formamide and dimethyformamide; sulfur-containing compounds such as dimethyl sulfoxide and sulfolane; imidazolidones such as 1,3-dimethyl-2-imidazolidone; ethers such as dioxane, 1,2-dimethoxyethane, and diglyme; halohydrocarbons such as dichloromethane, chloroform, and 1,2-dichloroethane; alcohols such as methanol and ethanol; aromatic hydrocarbons such as benzene and toluene; acid anhydrides such as acetic anhydride and propionic anhydride; and nitriles such as acetonitrile and propionitrile. Of these, acetonitrile is preferred in that it provides high solubility of these nitrosonium salt compounds. These organic solvents may be used alone or as a combination of two or more. Alternatively, water may be used in place of an organic solvent. However, use of water is limited to a reaction system such as $NO^+HSO_4^-$ and concentrated sulfuric acid, in that a nitrosonium salt compound is rapidly hydrolyzed with water. The solvent is preferably used in an amount by weight of 5–100 times that of the cyanobenzamide compound.

The reaction temperature preferably falls within the range of –30° C. to 100° C., more preferably within the range of –10° C. to 50° C. Excessively high reaction temperatures cause decomposition of the nitrosonium salt compound, whereas low reaction temperatures result in poor solubility of the cyanobenzamide compound, to thereby provide poor reactivity. Therefore, the reaction temperature is selected in consideration of achieving a balance between the stability of the nitrosonium salt and the solubility of the cyanobenzamide compound.

The reaction time is preferably 10 minutes to 10 hours, depending on the composition of the solvent.

Isolation and purification of the cyanobenzoic acid compound will next be described. The process typically employs an organic solvent. After completion of the reaction, the cyanobenzoic acid compound formed is precipitated or still remains dissolved in the solvent, depending on the type of solvent employed. When the cyanobenzoic acid compound is precipitated, isolation and purification can be completed simply through the sequential steps of filtration, washing with water, and drying. When the formed cyanobenzoic acid compound still remains dissolved, the residual solvent is removed through distillation at low temperature under reduced pressure, and water is added to the resultant residue so as to precipitate the cyanobenzoic acid compound. The further work-up process is carried out in a manner similar to that described above. In this case as well, the cyanobenzoic acid compound produced has a purity corresponding to that of the starting cyanobenzamide compound.

(iv) Process Employing a Nitrogen Oxide

In this process, a cyanobenzamide compound and a solvent are placed in a reactor, and a nitrogen oxide gas is fed into the mixture with stirring. The resultant mixture is allowed to react under stirring at a predetermined temperature for a predetermined period of time.

The manner of feeding of the above materials in the reaction is not particularly limited, and is typically carried out under atmospheric pressure.

The cyanobenzamide compound employed in process (i) can also be used in process (iv).

The nitrogen oxide compound used in the process will next be described. In the present invention, the term "nitrogen oxide" refers to a compound consisting of nitrogen and oxygen. Examples of nitrogen oxide compounds include nitrogen monooxide, dinitrogen trioxide, nitrogen dioxide, dinitrogen tetraoxide, and dinitrogen pentoxide. A mixture of dinitrogen monooxide and nitrogen dioxide may also be used as the nitrogen oxide. Alternatively, there may be used exhaust gas which is generated during oxidation of cyclohexane with large amounts of nitric acid in the nylon industry and which contains a large amount of nitrogen oxide, to thereby design an economically advantageous process.

The nitrogen oxide is used in the process in an amount of 1 mol or more based on 1 mol of the cyanobenzamide compound.

In the process, an organic solvent or water can be used as a solvent system. An organic solvent is preferred in view of the solubility of a cyanobenzamide compound serving as a raw material. Examples of the usable organic solvents include polar amides such as formamide and dimethylformamide; sulfur-containing compounds such as dimethyl sulfoxide and sulfolane; imidazolidones such as 1,3-dimethyl-2-imidazolidone; ethers such as dioxane, 1,2-dimethoxyethane, and diglyme; halohydrocarbons such as dichloromethane, chloroform, and 1,2-dichloroethane; acid anhydrides such as acetic anhydride and propionic anhydride; and carboxylic acids such as acetic acid, trifluoroacetic acid, and propionic acid. These organic solvents may be used alone or as a combination of two or more. Of these organic solvents, polar organic solvents such as carboxylic acids, acid anhydrides, polar amides, and sulfur-containing compounds are preferred. An acetic acid-acetic anhydride mixture is particularly preferred.

When water is used as a solvent, the presence of a protonic acid promotes the reaction. Thus, an acidic aqueous solution containing an acid such as sulfuric acid, nitric acid, hydrochloric acid, or phosphoric acid may be used as a solvent. Preferably, an aqueous solution of sulfuric acid is used, particularly preferably an aqueous solution of sulfuric acid having a concentration of 50 wt. % or more.

When the reaction is carried out in an organic solvent, the presence of a base promotes the reaction. Examples of bases which can be employed include carboxylate salts such as sodium acetate and potassium acetate; and sulfonate salts such as sodium methanesulfonate and sodium p-toluenesulfonate. In this case, a solvent system of acetic acid-acetic anhydride-sodium acetate is particularly preferred.

The organic solvent employed in the process is used in an amount by weight of 5–100 times that of the cyanobenzamide compound. The reaction temperature preferably falls within the range of –80° C. to 100° C., more preferably within the range of –10° C. to 50° C. The reaction time is preferably 10 minutes to 10 hours, depending on the type of the solvent employed.

When an acidic aqueous solution is used as a solvent and the reaction temperature is very low, the rate of reaction decreases due to poor solubility of a cyanobenzamide compound serving as a raw material; whereas when the reaction temperature is excessively high, the nitrile group of the cyanobenzamide compound serving as a raw material and the nitrile group of the cyanobenzoic acid compound produced are both hydrated and hydrolyzed, to lower the yield of the target compound. Therefore, the reaction temperature is preferably 0–60° C., more preferably 5–30° C.

Isolation and purification of the cyanobenzoic acid compound will next be described. The process employs an organic solvent. After completion of the reaction, the formed cyanobenzoic acid compound is precipitated or still remains dissolved in the solvent, depending on the type of solvent employed. When the cyanobenzoic acid compound is precipitated, isolation and purification can be completed simply through the sequential steps of filtration, washing with water, and drying. When the formed cyanobenzoic acid compound still remains dissolved, the residual solvent is removed through distillation at low temperature under vacuum, and water is added to the resultant residue so as to precipitate the cyanobenzoic acid compound, which is further subjected to filtration, washing with water, and drying. In this case as well, the produced cyanobenzoic acid compound has a purity corresponding to that of the starting cyanobenzamide compound.

When the solvent is an acidic aqueous solution, the cyanobenzoic acid compound formed is precipitated due to considerably poor solubility thereof to the acidic aqueous solution. Thus, the precipitate is separated through filtration, washed with water, and dried, to thereby produce a cyanobenzoic acid compound having a purity corresponding to that of the starting cyanobenzamide compound.

(B) Process for Producing an Alkyl Cyanobenzoate Compound from a Phthalonitrile Compound as a Raw Material This process comprises two reaction steps:

(1) a first reaction step wherein a phthalonitrile compound is reacted with an aliphatic alcohol in the presence of an acid in a suitable amount to thereby transform exclusively one nitrile group into an alkylimino ether group; and (2) a second reaction step wherein a reaction mixture containing alkylimino ether (or a salt thereof) formed in the first reaction step, or wherein isolated alkylimino ether (or a salt thereof) is reacted with water to thereby produce an alkyl cyanobenzoate compound.

The process may employ the above-described phthalonitrile compound.

In the first reaction step, a $C_1$–$C_5$ aliphatic alcohol may be used as a reaction solvent. Examples of aliphatic alcohols having a $C_1$–$C_5$ alkyl group include methanol, ethanol, n-propanol, n-butanol, n-pentanol, isopropanol, isobutanol, sec-butanol, tert-butanol, isoamyl alcohol, active amyl alcohol, and neopentyl alcohol. Of these, methanol or ethanol is preferred.

The first reaction step may be carried out at atmospheric pressure or under pressurized conditions.

No particular limitation is imposed on the reaction temperature in the first reaction step, but the temperature preferably falls within a range of 0 to 200° C. Low reaction temperatures cause the reaction to proceed slowly so that the reaction requires a long time for completion, due to low solubility of a phthalonitrile compound in an aliphatic alcohol, which is unsatisfactory; whereas high reaction temperatures result in the alkylimino ether produced to decompose to thereby disadvantageously provide a low yield of the target compound.

The reaction time of the first reaction step falls within a range of 10 minutes to 48 hours, preferably one to 24 hours.

The reaction time should be appropriately adjusted in accordance with an aliphatic alcohol used in the reaction. A short reaction time results in low conversion of a phthalonitrile compound, whereas a long reaction time results in a low yield of the target and poor productivity.

An acid is used in the first reaction step wherein a nitrile group is transformed into an alkylimino ether group. Examples of acids which may be used in the step include inorganic acids such as hydrochloric acid, sulfuric acid, nitric acid, and phosphoric acid; organic acids such as formic acid and acetic acid; and Lewis acids such as ferrous chloride, ferric chloride, stannous chloride, and aluminum chloride. Of these, hydrochloric acid and concentrated sulfuric acid are preferred. These acids may be used alone or as a combination of two or more.

The acid is added in an amount of 0.1–5.0 mol based on 1 mol of the phthalonitrile compound, preferably 0.8–3 mol. A low amount results in poor reactivity and low yield of the target compound, whereas a high amount results in transformation of two nitrile groups of the phthalonitrile compound into two alkylimino ether groups, to thereby disadvantageously provide a low yield of the target compound.

In the second reaction step, an alkyl cyanobenzoate compound is produced by only the addition of water to the reaction mixture formed in the first reaction step. Also, the alkyl cyanobenzoate compound is produced by reacting water with the alkylimino ether (or a salt thereof) formed in the first reaction after isolation of the ether. In either case, water is added in an amount of preferably 0.8–20 mol based on 1 mol of the alkylimino ether (or a salt thereof). Amounts of less than 0.8 mol decrease the amount of the ether which is transformed into an alkyl ester group and reduce the yield of the target compound, whereas amounts in excess 20 of mol cause the alkyl cyanobenzoate compound to precipitate in the same way as in the case of an unreacted phthalonitrile compound, making these two compounds difficult to separate.

As compared with an alkylimino ether (or a salt thereof) or an alkyl cyanobenzoate compound, an unreacted phthalonitrile compound has low solubility to an aliphatic alcohol, and the compound may be recycled by means of filtration and reused in the reaction. Accordingly, the unreacted phthalonitrile compound may be recycled by means of filtration and reused in the reaction after the first reaction step and the second reaction step, since the compound does not dissolve in the reaction mixture.

After the second reaction step, a crude alkyl cyanobenzoate compound may be formed by cooling or concentrating the filtrate obtained by filtration of an unreacted phthalonitrile compound. Thus-obtained filtrate may be neutralized by use of an alkali. Examples of alkalis which may be used for neutralization include alkali metal hydroxides such as sodium hydroxide; alkali metal carbonates such as sodium carbonate; alkali metal phosphates such as trisodium phosphate; alkaline earth metal hydroxides such as calcium hydroxide; and ammonia. These alkalis may be used alone or as a combination of two or more.

Further, after the second reaction step, the filtrate obtained by filtration of an unreacted phthalonitrile compound may be extracted by use of an organic solvent and the extract may be concentrated, to thereby obtain crystals of an alkyl cyanobenzoate compound. Examples of organic solvents which may be used for extraction include hydrocarbons such as toluene and xylene, halo-hydrocarbons such as dichloromethane and chloroform, ethers such as diethyl ether, and esters such as ethyl acetate. Meanwhile, in accordance with need, the crystal may be purified by recrystallization making use of an aqueous solution of an aliphatic alcohol, or by distillation under reduced pressure. A small amount of the unreacted phthalonitrile compound may be removed by adsorption making use of active carbon.

(C) Process for Producing an Alkyl Cyanobenzoate Compound from a Cyanobenzamide Compound Serving as a Raw Material This process comprises reacting a cyanobenzamide compound with an aliphatic alcohol in the presence of an acid in a suitable amount to thereby transform exclusively the amide group into an alkyl ester group.

The above-described cyanobenzamide compound may be used in the process.

The above-described $C_1$–$C_5$ aliphatic alcohol is preferably used as an aliphatic alcohol in the process.

No particular limitation is imposed on the reaction temperature employed in the process, but the temperature preferably falls within a range of 0 to 100° C. Low reaction temperatures result in poor reactivity, whereas high reaction temperatures cause not only conversion of an amide group into an alkylester group but also transformation of the nitrile group into an alkylimino ether group, which is undesirable, to thereby provide a low yield of the target compound. In addition, the alkylimino ether group is reacted with water and easily transformed into an alkyl ester group, to thereby form dialkyl phthalate. Therefore, the alkyl cyanobezoate is not purified effectively, resulting in a low yield of the target compound.

The reaction time falls within a range of 10 minutes to 48 hours, preferably one to 24 hours. The reaction time may be appropriately adjusted in accordance with the aliphatic alcohol used in the reaction. Short reaction times cause low conversion of a cyanobenzamide compound, whereas long reaction times result in poor productivity.

Examples of acids which can be used for transforming the amide group into an alkyl ester group include inorganic acids such as hydrochloric acid, sulfuric acid, nitric acid, and phosphoric acid; organic acids such as formic acid and acetic acid; and Lewis acids such as ferrous chloride, ferric chloride, stannous chloride, and aluminum chloride. Of these, hydrochloric acid or sulfuric acid is preferred. These acids may be used alone or as a combination of two or more species.

The acid is added in amount of 0.1–7.0 mol based on 1 mol of the cyanobenzamide compound serving as a raw material, preferably 0.8–5.0 mol. Low amounts result in poor reactivity and low yield of the target compound; whereas excessive amounts cause transformation of the cyano group of the cyanobenzamide compound into an alkylimino ether group to thereby disadvantageously result in a low yield of the target compound. The above-described acid may be added directly to the reaction mixture, or may be added in the form of an alcohol solution produced by use of the same aliphatic alcohol of the reaction solvent.

After completion of the reaction, water is added directly to the reaction mixture and the mixture is heated so as to dissolve the water, and the reaction mixture is cooled to thereby obtain crystals of an alkyl cyanobenzoate. Alternatively, the reaction mixture is concentrated by means of removal of the solvent in order to increase the percent recovery, and water is added to the concentrated reaction mixture. In addition, an alkali may be added into the reaction mixture for neutralization, after which the mixture is subjected to crystallization or concentration. Examples of alkalis which may be used for neutralization include alkali metal hydroxides such as sodium hydroxide; alkali metal carbonates such as sodium carbonate; alkali metal phosphates such as trisodium phosphate; alkaline earth metal hydroxides such as calcium hydroxide; and ammonia. These alkalis may be used alone or as a combination of two or more at arbitrary ratios. Further, the reaction mixture may be extracted by use of an organic solvent and the extract concentrated, to thereby obtain crystals. Examples of organic solvents which may be used for extraction include hydrocarbons such as toluene and xylene, halo-hydrocarbons such as dichloromethane and chloroform, ethers such as diethyl ether, and esters such as ethyl acetate. In accordance with need, the alkyl cyanobenzoate thus-obtained may be purified by means of recrystallization or distillation under reduced pressure.

(D) Process for Producing a Cyanobenzoic Acid Compound from a Cyanobenzylamine Compound Serving as a Raw Material This process comprises reacting a cyanobenzylamine compound with an iron compound or a ruthenium compound, and with an oxidant (other than an iron compound or a ruthenium compound), and a base in accordance with need, in water or a mixture solvent of water and an aprotic polar solvent in a reaction vessel. The reaction proceeds with stirring at a predetermined temperature for a predetermined period of time.

The cyanobenzylamine compound used in the process is described below. Examples of unsubstituted cyanobenzylamine compounds include p-cyanobenzylamine and m-cyanobenzylamine, and these are synthesized by reduction of one nitrile group of terephthalonitrile and isophthalonitrile, respectively (JP-B-40-10133), and are easily obtained in large amounts.

Next, a description will be given of cyano-group-containing benzylamine compounds substituted by, for example, an alkyl group, an alkoxyl group, a halogen atom.

Cyanobenzylamine compounds substituted by halogen are described below. For example, chlorinated cyanobenzylamine compounds such as 4-cyano-2,3,5,6-tetrachlorobenzylamine and 3-cyano-2,4,5,6-tetrachlorobenzylamine are synthesized by reduction of one nitrile group of a chlorinated terephthalonitrile compound such as tetrachloroterephthalonitrile obtained by chlorination of terephthalonitrile, and one nitrile group of a chlorinated isophthalonitrile compound such as tetrachloroisophthalonitrile obtained by chlorination of isophthalonitrile. These chlorinated cyanobenzylamine compounds are easily obtained in large amounts. In addition, fluorinated cyanobenzylamine compounds such as 4-cyano-2,3,5,6-tetrafluorobenzylamine and 3-cyano-2,4,5,6-tetrafluorobenzylamine are synthesized by reduction of one nitrile group of a fluorinated terephthalonitrile compound such as tetrafluoroterephthalonitrile obtained by fluorination of a chlorinated terephthalonitrile compound such as tetrachloroterephthalonitrile, and one nitrile group of a fluorinated isophthalonitrile compound such as tetrafluoroisophthalonitrile obtained by fluorination of a chlorinated isophthalonitrile compound such as tetrachloroisophthalonitrile. These fluorinated cyanobenzylamine compounds are easily obtained in large amounts.

In the process, a ruthenium compound or an iron compound is used as an oxidation catalyst and an oxidant. A ruthenium compound such as ruthenium tetroxide ($RuO_4$) or an iron compound such as $Na_2FeO_4$ may be used alone for oxidation of a cyanobenzylamine compound. However, in consideration of cost and conservation of resources, an oxidant (hereinafter the term "an oxidant" refers to an oxidant other than an iron compound or a ruthenium compound) is preferably used for oxidation while an iron compound or a ruthenium compound is used as an oxidation catalyst. When an oxidant is used the process requires addition of a catalytic amount of a ruthenium compound or an iron compound.

When a ruthenium compound is used as an oxidation catalyst, an oxidant oxidizes a low-valence ruthenium compound such as ruthenium trichloride, to thereby form an active high-valence ruthenium compound. The high-valence ruthenium compound oxidizes a cyanobenzylamine compound to thereby produce a cyanobenzoic acid compound, and subsequently the high-valence ruthenium compound per se is reduced to the low-valence ruthenium compound. In the process, the oxidant repeatedly oxidizes the low-valence ruthenium compound into the active high-valence ruthenium compound, to thereby provide a catalyst cycle.

When an iron compound is used as an oxidation catalyst, an oxidant oxidizes a low-valence iron compound such as di- or tri-valent iron compound, to thereby form an active high-valence iron compound. The high-valence iron compound oxidizes a cyanobenzylamine compound to thereby produce a cyanobenzoic acid compound, and subsequently the high-valence iron compound per se is reduced to the low-valence iron compound. In the process, the oxidant repeatedly oxidizes the low-valence iron compound into the active high-valence iron compound, to thereby provide a catalyst cycle.

When an iron compound is used as an oxidation catalyst, an oxidant oxidizes a low-valence iron compound such as di- or tri-valent iron compound, to thereby form an active high-valence iron compound. The high-valence iron compound oxidizes a cyanobenzylamine compound to thereby produce a cyanobenzoic acid compound, and then the high-valence iron compound per se is reduced into the low-valence iron compound. In the process, the oxidant repeatedly oxidizes the low-valence iron compound in to the active high-valence iron compound, to thereby provide a catalyst cycle.

Examples of ruthenium compounds which may be used as an oxidation catalyst in the process employing an oxidant include ruthenium inorganic salts such as ruthenium tetroxide, ruthenium trichloride, ruthenium tribromide, ruthenium triiodide, ruthenium hydroxide, ruthenium oxide, and ruthenium nitrosyl nitrate and ruthenium complexes such as ruthenium acetylacetonato and dodecacarbonyl triruthenium.

Examples of iron compounds which may be used as an oxidation catalyst in the process employing an oxidant include ferrous chloride, ferric chloride, ferrous bromide, ferric bromide, ferrous iodide, ferric iodide, ferrous oxide, ferric oxide, ferrosoferric oxide ($Fe_3O_4$), ferrous hydroxide, ferric hydroxide, iron (III) oxyhydroxide (FeO(OH)), ferrous sulfide, ferric sulfide, iron disulfide, ferrous sulfate, ferric sulfate, ferrous nitrate, ferric nitrate, iron carbonate, ferrous thiocyanate, ferric thiocyanate, ferrous acetate, ferrous oxalate, and ferric oxalate.

The mol ratio of ruthenium compound or iron compound, which may be used as an oxidation catalyst in the process employing an oxidant, to the cyanobenzylamine compound is preferably 0.001–0.05.

No particular limitation is imposed on the oxidant which may be used in the process, so long as the oxidant is capable of oxidizing a ruthenium compound or an iron compound. Examples of such oxidants include basic hypohalogenous acid compounds and persulfates.

Examples of hypohalogenous acid compounds which may be used in the process include hypohalogenous acids such as hypochlorous acid, hypobromous acid, and hypoiodous acid and hypohalogenous acid salts such as sodium hypochlorite, potassium hypochlorite, calcium hypochlorite, barium hypochlorite, sodium hypobromite, potassium hypobromite, sodium hypoiodite, and potassium hypoiodite. Examples of persulfates which may be used in the process include ammonium persulfate, sodium persulfate, and potassium persulfate.

The oxidant used in the process may be added in one portion at the beginning of the reaction, or may be gradually added so that the reaction does not proceed rapidly. The mol ratio of the oxidant to the cyanobenzylamine compound is preferably 3–6.

The process is performed in a basic atmosphere. In a basic atmosphere, reoxidation of a ruthenium compound or an iron compound may be performed at a sufficient rate. In the process, a cyanobenzoic acid compound is produced in accordance with oxidation of a cyanobenzylamine compound, and the reaction mixture has acidity, and therefore a base is added to the mixture in order to maintain the basicity. In the process, the required amount of the base may be added in one portion at the beginning of the reaction, or the base may be added successively during the reaction so as to maintain the basicity of the mixture.

The pH of the reaction mixture is described below. When the mixture is strongly basic, the cyano group of a cyanobenzylamine compound serving as a raw material and the cyano group of a cyanobenzoic acid compound serving as the target compound may decompose; whereas when the mixture is acidic, the reaction proceeds slowly and involves many side reactions. Therefore, the pH of the reaction is preferably 7.5–12.

Examples of bases which may be used in the process include alkali metal hydroxides and alkaline earth metal hydroxides such as lithium hydroxide, sodium hydroxide, potassium hydroxide, magnesium hydroxide, and calcium hydroxide; alkali metal bicarbonates such as sodium bicarbonate and potassium bicarbonate; alkali metal carbonates and alkaline earth metal carbonates such as lithium carbonate, sodium carbonate, potassium carbonate, magnesium carbonate, and calcium carbonate; and alkali and alkaline earth metal oxides such as magnesium oxide and calcium oxide. The amount of the base used for the above-described object depends on the type and the amount of an oxidant which coexists with the base, but the minimum amount is required in order to maintain the basicity of the reaction mixture throughout the entire process. When a hypochlorous acid compound is used as an oxidant, two types of bases are necessary, i.e., a base which is used for the formation of a basic hypochlorous acid compound from the hypochlorous acid compound, and a base which is used for the formation of a carboxylic acid salt from the produced cyanobenzoic acid compound. The mol ratio of monovalent base to cyanobenzylamine compound is preferably 3–6.

When a persulfate is used as an oxidant, two types of bases are required; i.e., a base which is used for formation of a sulfate from a hydrogensulfate produced by reduction of the persulfate, and a base which is used for formation of a carboxylic acid salt from the produced cyanobenzoic acid compound. The mol ratio of monovalent base to cyanobenzylamine compound is preferably 7–13.

The solvent used in the process is described below. The reaction may be performed in an aqueous solution. Moreover, a water-insoluble intermediate may be produced in accordance with oxidation of a cyanobenzylamine compound, and therefore an aprotic polar solvent is also used in the reaction in order to partially dissolve the intermediate contained therein. Consequently, the reaction may proceed effectively. Examples of aprotic polar solvents which may be used in the process include ethers such as dioxane and diglyme; amides such as dimethylformamide; sulfur-containing solvents such as dimethyl sulfoxide and sulfolane; and nitrile-solvents such as acetonitrile. In the present process, the aprotic polar solvent is used in an amount by weight of at least five times that of the cyanobenzylamine compound, and the solvent is used within a range where the solvent can be mixed with water. Preferably, the solvent is used in an amount of 5–20 times that of the cyanobenzylamine compound on a weight basis.

An excessively low reaction temperature causes the reaction to proceed slowly, whereas a high reaction temperature causes decomposition of the nitrile group of a cyanobenzylamine compound, and therefore the temperature is preferably 0–80° C., more preferably 10–50° C. The reaction time depends on the nature of the solvent employed, but preferably falls within a range of 10 minutes to 15 hours.

When a surplus of an oxidant such as a hypochlorous acid compound remains in the reaction mixture after completion of the reaction, in accordance with need, urea may be added into the mixture for decomposition of the surplus.

Isolation and purification of a cyanobenzoic acid compound are described below. After completion of the reaction, the cyanobenzoic acid compound exists in an aqueous solution in the form of a carboxylic acid salt. Depending on its type, the salt may dissolve or precipitate in the solution. The solubility of the cyanobenzoic acid compound in water is very low, and the compound precipitates in the solution by mere addition of an acid thereto. Therefore, the solution is simply filtered and washed with water and then dried, to thereby obtain the cyanobenzoic acid compound, and the purity of thus-produced compound reflects the purity of a cyanobenzylamine compound serving as a raw material.

(E) Process for Producing a Cyanobenzoic Acid Compound from an Alkyl Cyanobenzoate Compound Serving as a Raw Material This process comprises transforming, in the presence of a base for adjusting pH, exclusively an alkyl ester group of an alkyl cyanobenzoate compound into a carboxyl group while the cyano group in the compound remains, to thereby produce a cyanobenzoic acid salt, and adding an acid to thereby obtain a cyanobenzoic acid compound.

The process may employ the above-described alkyl cyanobenzoate compound represented by formula (I).

Among the above-described compounds, examples of unsubstituted alkyl cyanobenzoate compounds which may preferably be used include p-methyl cyanobenzoate, p-ethyl cyanobenzoate, m-methyl cyanobenzoate, and m-ethyl cyanobenzoate.

In addition, examples of substituted alkyl cyanobenzoate compounds include methyl 2,3,5,6-tetrachloro-4-cyanobenzoate, ethyl 2,3,5,6-tetrachloro-4-cyanobenzoate, methyl 2,4,5,6-tetrachloro-3-cyanobenzoate, ethyl 2,4,5,6-tetrachloro-3-cyanobenzoate, methyl 2,3,5,6-tetrafluoro-4-cyanobenzoate, ethyl 2,4,5,6-tetrafluoro-3-cyanobenzoate, methyl 3-chloro-5-cyano-2,4,6-trifluorobenzoate, and ethyl 3-chloro-5-cyano-2,4,6-trifluorobenzoate.

The process employs an aqueous solution containing a water-soluble organic solvent. The concentration of the organic solvent in the aqueous solution is preferably 20–70%. Low concentrations lower the solubility of an alkyl cyanobenzoate compound so that the reaction requires a long time for completion, whereas high concentrations lower reactivity due to a low concentration of water in the solution, so that the reaction requires a long time for completion, which is unsatisfactory.

Examples of water-soluble organic solvents which may be used in the process include alcohol solvents, ether solvents, and nitrogen-containing solvents. Of these, examples of alcohol solvents include methanol, ethanol,- n-propanol, n-butanol, n-pentanol, isopropanol, isobutanol, sec-butanol, tert-butanol, isoamyl alcohol, neopentyl alcohol, ethylene glycol, and propylene glycol. Examples of ether solvents include dioxane, tetrahydrofuran, ethylene glycol dimethyl ether, ethylene glycol diethyl ether, diethylene glycol dimethyl ether, and diethylene glycol diethyl ether. Examples of nitrogen-containing solvents include N,N-dimethylformamide, N,N-diethylformamide, N,N-dimethylacetamide, and N-methylpyrrolidone.

The reaction temperature preferably falls within a range of 0–100° C. Low reaction temperatures lower reactivity and cause the reaction to require a large amount of a base, whereas high reaction temperatures cause transformation of both an alkyl ester group and the nitrile group of an alkyl cyanobenzoate compound, to thereby disadvantageously produce a large amount of impurities.

The reaction time falls within a range of 10 minutes to 48 hours, preferably one to 24 hours. The reaction time may be appropriately adjusted in accordance with the pH of the reaction mixture, the reaction temperature, and the type of organic solvent employed in the reaction. Short reaction times lower the conversion of an alkyl cyanobenzoate compound, whereas long reaction times lower the yield of the target compound and result in poor productivity, which is unsatisfactory.

Examples of bases which may be used in the process include alkali metal hydroxides such as sodium hydroxide, alkali metal carbonates such as sodium carbonate, alkali metal phosphates such as trisodium phosphate, alkaline earth metal hydroxides such as calcium hydroxide, and ammonia. Of these, alkali metal hydroxides and carbonates are preferred.

These base ingredients may be used alone or in combination of two or more at arbitrary ratios. In the reaction mixture, a base may be added in the form of a solid, and is preferably added in the form of an aqueous solution thereof. The amount by mol of the base is preferably equivalent to the amount by mol of an alkyl cyanobenzoate compound.

When an alkyl ester group of an alkyl cyanobenzoate compound is transformed into a carboxyl group, the pH of the reaction mixture is preferably maintained at 8–12. The pH may be adjusted appropriately, since a suitable pH depends on the reaction temperature. A very low pH reduces reactivity so that the reaction requires a long time for completion, whereas a very high pH results in hydrolyzation of both the alkyl ester group and the nitrile group of the alkyl cyanobenzoate compound, after which they are transformed into an amide group or a carboxyl group, to thereby disadvantageously provide a low yield of the target compound. In addition, phthalamic acid thus-produced or terephthalic acid is difficult to remove, since the acid is included in crystals during the process of recrystallization due to its low solubility to the reaction mixture, which is unsatisfactory in consideration of purity of the target compound.

After completion of reaction, crystals of cyanobenzoic acid compound are precipitated by addition of an acid. Examples of acids which may be used for acid precipitation include inorganic acids such as hydrochloric acid, sulfuric acid, nitric acid, and phosphoric acid; and organic acids such as formic acid and acetic acid. These acids may be used singly or in combination of two or more species at arbitrary ratios. When an acid is added to the reaction mixture, the pH of the mixture is preferably adjusted so that the pH becomes lower than the pKa of the cyanobenzoic acid compound.

After completion of the precipitation, crystals of a cyanobenzoic acid compound thus-obtained are heated for dissolution. When the crystals of the compound dissolve incompletely, an organic solvent is added to the mixture. Subsequently, the mixture is cooled to thereby recrystallize the compound. In accordance with need, the compound may be subjected to recrystallization by use of an alcoholic aqueous solution, to thereby prepare highly pure crystals of the cyanobenzoic acid compound.

(F) Process for Producing a Cyanobenzoyl Chloride Compound from a Cyanobenzoic Acid Compound Serving as a Raw Material This process comprises reacting a cyanobenzoic acid compound with phosgene or a precursor thereof and stirring the reaction mixture at a predetermined temperature for a predetermined period of time. In order to promote the reaction, an additive such as a cyanobenzoyl chloride compound corresponding to the cyanobenzoic acid compound, a tertiary amide compound, or a tertiary amine compound may be incorporated into the reaction system in the presence of an organic solvent.

The cyanobenzoic acid compound used in the process will next be described. Examples of unsubstituted cyanobenzoic acid compounds include p-cyanobenzoic acid and m-cyanobenzoic acid. These compounds may be synthesized through a known method or through the process of the present invention.

The halo-substituted cyanobenzoic acid compound will next be described. Chlorinated cyanobenzoic acid compounds such as 4-cyano-2,3,5,6-tetrachlorobenzoic acid and 3-cyano-2,4,5,6-tetrachlorobenzoic acid may be synthesized from a chlorinated terephthalonitrile compound such as tetrachloroterephthalonitrile or a chlorinated isophthalonitrile compound such as tetrachloroisophthalonitrile, through a known method or through the process of the present invention.

Fluorinated cyanobenzoic acid compounds such as 4-cyano-2,3,5,6-tetrafluorobenzoic acid and 3-cyano-2,4,5,6-tetrafluorobenzoic acid may be synthesized through a known method or through the process of the present invention, by use of a fluorinated tetrephthalonitrile compound such as tetrafluoroterephthalonitrile or a fluorinated isophthalonitrile compound such as tetrafluoroisophthalonitrile, which is obtained through fluorination of the corresponding chlorinated species.

Phosgene or a precursor thereof used in the process will next be described. Phosgene may be introduced to the reaction system in the form of a gas or liquid produced through pressurization or cooling.

The phosgene gas is used in an amount of at least equiomol based on the cyanobenzoic acid compound, preferably 1.1–4 mol based on 1 mol of the cyanobenzoic acid compound, more preferably, 1.1–1.5 mol, with unreacted phosgene gas being recycled.

The reaction between phosgene and a cyanobenzoic acid compound will next be described in detail. When a phosgene monomer is employed, the monomer is reacted directly with a cyanobenzoic acid compound. As the reaction proceeds, carbon dioxide and hydrochloric acid are formed during formation of the corresponding cyanobenzoyl chloride compound. Phosgene is typically introduced into the reaction system until the phosgene is no longer consumed and formation of carbon dioxide and hydrochloric acid is completed. A precursor of phosgene is easily converted to phosgene with heat or through a treatment with a catalyst. Active carbon may be used as the catalyst. Examples of precursors include a dimer and a trimer of phosgene. The phosgene dimer may directly be introduced to a reactor. Alternatively, the dimer may be converted to phosgene gas in another reactor, and the gas formed may be introduced to the reactor. The phosgene trimer, which is solid at room temperature, may be fed to the reactor in a required amount in one portion or may be fed to the reactor in the form of a solution after dissolution in an inert solvent.

A method for isolating the formed cyanobenzoyl chloride compound will next be described. In accordance with needs, excessive phosgene and hydrochloric acid remaining in the reaction mixture are removed through a method such as heating or bubbling of an inert gas; e.g., nitrogen. When a solvent is used, the solvent is removed through distillation. The cyanobenzoyl chloride compound formed can be isolated from the reaction mixture through a customary method, such as distillation or crystallization.

In general, a cyanobenzoic acid compound has poor solubility to an organic solvent. Therefore, a cyanobenzoyl chloride compound corresponding to the cyanobenzoic acid compound is added during the reaction, or is used as a solvent, to thereby enhance reaction efficiency. In this case, the cyanobenzoyl chloride compound and the cyanobenzoic acid compound may be mixed with each other directly, or with an inert solvent when stirring is difficult. The cyanobenzoyl chloride compound provides an effect of promoting the reaction.

The process employs an aprotic organic solvent. Examples of such organic solvents include nitriles such as acetonitrile; tertiary formamides such as dimethylformamide and diethyformamide; sulfur-containing compounds such as sulforane; imidazolidones such as 1,3-dimethyl-2-imidazolidone; ethers such as dioxane, 1,2-dimethoxyethane, and diglyme; halohydrocarbons such as dichloromethane, chloroform, and 1,2-dichloroethane; and aromatic hydrocarbons such as benzene, toluene, and o-, m-, p-, and mixed xylene. These organic solvents may be used alone or as a combination of two or more.

The reaction time is preferably 10 minutes to 10 hours, depending on the composition of the employed solvent.

The process may employ additives so as to promote reaction. Examples of such additives include tertiary formamides such as dimethylformamide, diethylformamide, dimethylpropionamide, and dibutylformamide. When used, the amount of tertiary formamide is at least 0.01 mol equivalents based on the carboxylic acid.

A tertiary amine compound may be added as a reaction promoter. The tertiary amine compound functions as a catalyst for activating phosgene or as a scavenger of hydrochloric acid formed during transformation of a cyanobenzoic acid to its acid chloride. Preferred examples of the tertiary amine compound include aliphatic tertiary amines such as trimethylamine, triethylamine, and tribenzylamine; aromatic tertiary amines such as triphenylamine and tri-p-toluylamine; and heterocyclic compounds such as imidazole, pyridine, p-dimethylaminopyridine, N-methylmorpholine, quinoline, isoquinoline, pyrimidine, and piperazine. When used as a catalyst for activating phosgene, the tertiary amine compound is used in an amount of at least 0.01 mol equivalents based on the carboxylic acid. When the amine compound is used for activating phosgene and as a scavenger of hydrochloric acid, the amine compound must be used in an amount of at least equimol to phosgene employed in the reaction.

EXAMPLES

The present invention will next be described in more detail by way of examples, which should not be construed as limiting the invention thereto. Unless otherwise indicated, all parts, percents, ratios and the like are by weight.

In Examples 1 to 31 and 45 to 59, high performance liquid chromatographic analysis was carried out under the following conditions.

HPLC Analysis Conditions
Column: Shodex (registered trademark: Showa Denko K.K.) DE-513L+precolumn Column temperature: 40° C.
Eluent: water/acetonitrile/acetic acid=2250/750/15 (ml) sodium 1-octanesulfonate 6.45 g
Flow rate 1 ml/minute
Detector: UV 254 nm In Examples 32 to 44 and 60 to 65, gas chromatographic analysis was carried out under the following conditions.

GC Analysis Conditions
Column: DB1 (J&W)
(30m capillary column, inside diameter 0.32 mm)
Carrier: helium 3 cc/minute
Split ratio: 40
Detector: FID
Analysis conditions: injection at 300° C.
100° C. (10 minutes)→15° C./minute
(elevation)→280° C. (8 minutes)
detection at 300° C.

Example 1

Terephthalonitrile (12.8 g, 0.1 mol) and methanol (170.1 g) were mixed, and the resultant mixture was heated to 64° C. with stirring. To the mixture, a 20% aqueous solution of sodium hydroxide (12 g) was added over six hours. Liquid chromatographic analysis revealed the reaction mixture contained 9.1 g of p-cyanobenzamide (yield 62%).

Example 2

Terephthalonitrile (12.8 g, 0.1 mol) and ethanol (170.1 g) were mixed, and the resultant mixture was heated to 79° C. with stirring. To the mixture, a 20% aqueous solution of sodium hydroxide (4 g) was added over six hours. Liquid chromatographic analysis revealed the reaction mixture contained 9.6 g of p-cyanobenzamide (yield 66%).

Example 3

Terephthalonitrile (12.8 g, 0.1 mol) and ethanol (170.1 g) were mixed, and the resultant mixture was heated to 50° C. with stirring. To the mixture, a 20% aqueous solution of sodium hydroxide (10 g) was added over six hours. Liquid chromatographic analysis revealed the reaction mixture contained 9.6 g of p-cyanobenzamide (yield 66%).

Example 4

Terephthalonitrile (12.8 g, 0.1 mol) and ethanol (170.1 g) were mixed, and the resultant mixture was heated to 30° C. with stirring. To the mixture, a 20% aqueous solution of sodium hydroxide (10 g) was added over six hours. Liquid chromatographic analysis revealed the reaction mixture contained 9.8 g of p-cyanobenzamide (yield 67%).

Example 5

Terephthalonitrile (12.8 g, 0.1 mol) and isopropanol (243.2 g) were mixed, and the resultant mixture was heated to 80° C. with stirring. To the mixture, a 20% aqueous solution of sodium hydroxide (4 g) was added over three hours. Liquid chromatographic analysis revealed the reaction mixture contained 10.8 g of p-cyanobenzamide (yield 74%).

Example 6

Terephthalonitrile (12.8 g, 0.1 mol) and n-butanol (243.2 g) were mixed, and the resultant mixture was heated to 80° C. with stirring. To the mixture, a 20% aqueous solution of sodium hydroxide (4 g) was added over three hours. Liquid chromatographic analysis revealed the reaction mixture contained 9.9 g of p-cyanobenzamide (yield 68%).

Example 7

Terephthalonitrile (12.8 g, 0.1 mol) and isobutanol (243.2 g) were mixed, and the resultant mixture was heated to 80° C. with stirring. To the mixture, a 20% aqueous solution of sodium hydroxide (4 g) was added over three hours. Liquid chromatographic analysis revealed the reaction mixture contained 9.6 g of p-cyanobenzamide (yield 66%).

Example 8

Terephthalonitrile (12.8 g, 0.1 mol) and sec-butanol (243.2 g) were mixed, and the resultant mixture was heated to 80° C. with stirring. To the mixture, a 20% aqueous solution of sodium hydroxide (4 g) was added over three hours. Liquid chromatographic analysis revealed the reaction mixture contained 10.7 g of p-cyanobenzamide (yield 73%).

Example 9

Terephthalonitrile (12.8 g, 0.1 mol) and tert-butanol (243.2 g) were mixed, and the resultant mixture was heated to 80° C. with stirring. To the mixture, a 20% aqueous solution of sodium hydroxide (4 g) was added over three hours. Liquid chromatographic analysis revealed the reaction mixture contained 12.6 g of p-cyanobenzamide (yield 86%).

Example 10

Terephthalonitrile (12.8 g, 0.1 mol) and tert-butanol (243.2 g) were mixed, and the resultant mixture was heated to 80° C. with stirring. To the mixture, a 26% aqueous solution of potassium hydroxide (4.3 g) was added over three hours. Liquid chromatographic analysis revealed the reaction mixture contained 11.8 g of p-cyanobenzamide (yield 81%).

Example 11

Isophthalonitrile (12.8 g, 0.1 mol) and methanol (115.2 g) were mixed, and the resultant mixture was heated to 64° C. with stirring. To the mixture, a 20% aqueous solution of sodium hydroxide (10 g) was added over six hours. Liquid chromatographic analysis revealed the reaction mixture contained 13.1 g of m-cyanobenzamide (yield 90%).

Example 12

The p-cyanobenzamide synthesized by the method as described in Example 9 was neutralized with sulfuric acid, and concentrated under reduced pressure so as to remove the solvent. Water was added to the concentrated p-cyanobenzamide so as to precipitate crystals of p-cyanobenzamide. The crystals were separated through filtration, washed with water, and dried, to thereby obtain 12.4 g of p-cyanobenzamide. Liquid chromatographic analysis revealed that the obtained p-cyanobenzamide had a purity of 95% (yield 81%).

Example 13

Tetrachloroterephthalonitrile (26.6 g, 0.1 mol) and ethanol (532 g) were mixed, and the resultant mixture was heated to 79° C. with stirring. To the mixture, a 20% aqueous solution of sodium hydroxide (16 g) was added over six hours. Liquid chromatographic analysis revealed the reaction mixture contained 16.5 g of 2,3,5,6-tetrachloro-4-cyanobenzamide (yield 58%).

Example 14

Terephthalonitrile (128 g) and tert-butanol (2432 g) were placed in a four-neck flask, and the mixture was heated to 80° C. with stirring. To the mixture, a 20% aqueous solution (13.4 g) of sodium hydroxide was added over three hours by use of a tube pump. Liquid chromatographic analysis revealed that the reaction mixture contained 71.5 g of p-cyanobenzamide (yield 49%) and 64 g of terephthalonitrile (conversion 50%). The reaction mixture was cooled to 25° C., neutralized with concentrated sulfuric acid (98% by weight), and heated under reduced pressure so as to concentrate the mixture and to remove tert-butanol (1824 g). After normal pressure was restored, the mixture was cooled to 25° C., and water (540 g) was added thereto. Subsequently, an aqueous solution (887.5 g) of sodium hypochlorite (effective chlorine 12%) was added to the reaction mixture over six hours while a 50% aqueous solution of sulfuric acid was added so as to maintain the pH of the mixture at 5–6. Liquid chromatographic analysis revealed that the reaction mixture contained 69.1 g of crude p-cyanobenzoic acid (yield 47%) and terephthalonitrile (64 g). Subsequently, the residual solvent (1090 g) was removed from the reaction mixture through distillation under reduced pressure. To the resultant mixture, a 48% aqueous solution of sodium hydroxide was added to thereby adjust the pH to 8, and the terephthalonitrile precipitated (60.2 g) was recovered through filtration. To the filtrate, concentrated sulfuric acid was added so as to adjust the pH to 3.0 and precipitate p-cyanobenzoic acid from its salt. The precipitate was dissolved by adding methanol (309 g) with heat, and the solution was cooled for crystallization, to thereby obtain 60.0 g of p-cyanobenzoic acid having a purity of 98% (yield 40%).

Example 15

Terephthalonitrile (128 g) and ethanol (1700 g) were placed in a four-neck flask, and the mixture was heated to 78° C. with stirring. To the mixture, a 20% aqueous solution (10 g) of sodium hydroxide was added over three hours by use of a tube pump. Liquid chromatographic analysis revealed that the reaction mixture contained 71.5 g of p-cyanobenzamide (yield 40%) and 38.4 g of terephthalonitrile (conversion 70%). The reaction mixture was cooled to 25° C., neutralized with concentrated sulfuric acid, and heated under reduced pressure so as to concentrate the mixture and to remove ethanol (1275 g). After normal pressure was restored, the mixture was cooled to 25° C., and water (720 g) was added thereto. Subsequently, an aqueous solution (887.5 g) of sodium hypochlorite (effective chlorine 12%) was added to the reaction mixture over six hours while a 50% aqueous solution of sulfuric acid was added so as to maintain the pH of the mixture at 5–6. Liquid chromatographic analysis revealed that the reaction mixture contained 55.9 g of crude p-cyanobenzoic acid (yield 38%) and terephthalonitrile (38 g). Subsequently, the residual solvent (1090 g) was removed from the reaction mixture through distillation under reduced pressure. To the resultant mixture, a 48% aqueous solution of sodium hydroxide was added to thereby adjust the pH to 8, and precipitated terephthalonitrile (36 g) was recovered through filtration. To the filtrate, concentrated sulfuric acid was added so as to adjust the pH to 3.0 and precipitate p-cyanobenzoic acid from its salt. The precipitate was dissolved by adding ethanol (309 g) with heat, and the solution was cooled for crystallization, to thereby obtain 52.6 g of p-cyanobenzoic acid having a purity of 95% (yield 34%).

Example 16

Isophthalonitrile (128 g) and ethanol (1700 g) were placed in a four-neck flask, and the mixture was heated to 78° C. with stirring. To the mixture, a 20% aqueous solution (10 g) of sodium hydroxide was added over three hours by use of a tube pump. Liquid chromatographic analysis revealed that the reaction mixture contained 100.7 g of p-cyanobenzamide (yield 69%) and 38.4 g of terephthalonitrile (conversion 70%). The reaction mixture was cooled to 25° C., neutralized with concentrated sulfuric acid, and heated under reduced pressure so as to concentrate the mixture and to remove ethanol (1275 g). After normal pressure was restored, the mixture was cooled to 25° C., and water (720 g) was added thereto. Subsequently, an aqueous solution (887.5 g) of sodium hypochlorite (effective chlorine 12%) was added to the reaction mixture over six hours while a 50% aqueous solution of sulfuric acid was added so as to maintain the pH of the mixture at 5–6. Liquid chromatographic analysis revealed that the reaction mixture contained 100.0 g of crude p-cyanobenzoic acid (yield 68%) and terephthalonitrile (38 g). Subsequently, the residual solvent (1090 g) was removed from the reaction mixture through distillation under reduced pressure. To the resultant mixture, a 48% aqueous solution of sodium hydroxide was added to thereby adjust the pH to 8, and precipitated terephthalonitrile (36 g) was recovered through filtration. To the filtrate, concentrated sulfuric acid was added so as to adjust the pH to 3.0 and precipitate p-cyanobenzoic acid from its salt. The precipitate was dissolved by adding ethanol (309 g) with heat, and the solution was cooled for crystallization, to thereby obtain 90.6 g of m-cyanobenzoic acid having a purity of 99% (yield 61%).

Example 17 p-Cyanobenzamide (146 g) which had been synthesized separately and water (584 g) were placed in a four-neck flask, and the mixture was cooled to 15° C. with stirring. Subsequently, an aqueous solution (1775 g) of sodium hypochlorite (effective chlorine 12%) was added to the reaction mixture over six hours while a 50% aqueous solution of sulfuric acid was added so as to maintain the pH of the mixture at 5–6. Liquid chromatographic analysis revealed that the reaction mixture contained 145.5 g of crude p-cyanobenzoic acid (yield 99%). To the reaction mixture, concentrated sulfuric acid was added so as to adjust the pH to 3.0 and precipitate p-cyanobenzoic acid from its salt. The precipitate was dissolved by adding methanol (820 g) with heat, and the solution was cooled for crystallization, to thereby obtain 138.9 g of p-cyanobenzoic acid having a purity of 99.5% (yield 94%).

Example 18

4-Cyano-2,3,5,6-tetrachlorobenzamide (284 g) which had been synthesized separately and water (2556 g) were placed in a four-neck flask, and the mixture was cooled to 15° C. with stirring. Subsequently, an aqueous solution (2360 g) of sodium hypochlorite (effective chlorine 12%) was added to the reaction mixture over six hours while a 50% aqueous solution of sulfuric acid was added so as to maintain the pH of the mixture at 5–6. Liquid chromatographic analysis revealed that the reaction mixture contained 262.2 g of 4-cyano-2,3,5,6-tetrachlorobenzoic acid (yield 92%).

Example 19

Sodium nitrite (2.07 g) was dissolved in a 70 wt. % aqueous sulfuric acid solution (100 ml), and p-cyanobenzamide (2.92 g) was added to the resultant solution. The mixture was allowed to react at room temperature for one hour with stirring. The precipitated crystals were collected through filtration, washed with water, and dried, to thereby obtain 2.77 g of p-cyanobenzoic acid (yield 95%). High performance liquid chromatographic analysis revealed that the p-cyanobenzoic acid obtained had a purity of 99% or more.

Example 20

Sodium nitrite (2.07 g) was dissolved in a 70 wt. % aqueous sulfuric acid solution (100 ml), and m-cyanobenzamide (2.92 g) was added to the resultant solution. The mixture was allowed to react at 40° C. for one hour with stirring. The precipitated crystals were collected through filtration, washed with water, and dried, to thereby obtain 2.68 g of m-cyanobenzoic acid (yield 92%). The m-cyanobenzoic acid obtained had a purity of 99% or more.

Example 21 p-Cyanobenzamide (1.46 g) and acetic acid (20 ml) were mixed and stirred vigorously at room temperature. To the mixture, sodium nitrite (2.07 g), and immediately thereafter, 95 wt. % sulfuric acid (3 g) was added and stirred vigorously for one hour. The acetic acid was removed under reduced pressure, and water (40 ml) was added to the residue. The precipitated crystals were collected through filtration, washed with water, and dried, to thereby obtain 1.26 g of p-cyanobenzoic acid (yield 86%). The p-cyanobenzoic acid obtained had a purity of 95%.

Example 22 p-Cyanobenzamide (14.6 g), sodium nitrite (20.7 g), acetic acid (200 ml), and acetic anhydride (20 ml) were mixed and stirred vigorously at 5° C. To the mixture, trifuloroacetic acid (35 g) was added dropwise over three hours, and further stirred vigorously for five hours. The solvent was removed under reduced pressure, and water (300 ml) was added to the residue. The precipitated crystals were collected through filtration, washed with water, and dried, to thereby obtain 13.4 g of p-cyanobenzoic acid (yield 92%). The p-cyanobenzoic acid obtained had a purity of 98%.

Example 23 m-Cyanobenzamide (2.92 g), sodium nitrite (2.76 g), and dimethyl sulfoxide (50 ml) were mixed and stirred vigorously at room temperature. To the mixture, methanesulfonic acid (3.95 g) was added dropwise over ten minutes, and further stirred vigorously for three hours. The solvent was removed under reduced pressure, and water (50 ml) was added to the residue. The precipitated crystals were collected through filtration, washed with water, and dried, to thereby obtain 2.57 g of m-cyanobenzoic acid (yield 88%). The obtained m-cyanobenzoic acid had a purity of 96%.

Example 24

Isophthalonitrile (2.56 g) and 50 wt. % sulfuric acid (100 ml) were mixed, and the resultant mixture was stirred vigorously at 70° C. Sodium nitrite (8.6 g) was added portionwise to the mixture over one hour. Formed crystals were collected through filtration, and water was added to the crystals. Sodium hydroxide was added to the solution under cooling with ice so as to adjust the pH of the solution to 8. After insoluble matter was removed through filtration, concentrated sulfuric acid was added to the filtrate under cooling with ice so as to adjust the pH of the filtrate to 6. The precipitated crystals were collected through filtration, and concentrated sulfuric acid was added to the filtrate again so as to adjust the pH of the filtrate to 6, to thereby collect precipitated crystals through filtration. The above process was repeated three times. The crystals obtained were combined, washed with water, and dried, to thereby obtain 1.53 g of m-cyanobenzoic acid (yield 52%). The m-cyanobenzoic acid obtained had a purity of 93%.

Example 25

Terephthalonitrile (12.8 g), sodium hydroxide (2.4 g), water (1.5 g), tert-butyl alcohol (300 ml) were mixed, and the resultant mixture stirred vigorously at 80° C. After the solvent was removed through distillation, sodium nitrite (16.6 g), acetic acid (250 ml), and acetic anhydride (25 ml) were added to the residue, and the resultant mixture was stirred vigorously at 5° C. Trifluoroacetic acid (27 g) was added dropwise to the mixture over three hours, and the mixture was further stirred vigorously for five hours. The solvent was removed through distillation under reduced pressure, and water (500 ml) was added to the residue. Sodium hydroxide was added to the solution under cooling with ice so as to adjust the pH to 8. After insoluble matter was removed through filtration, concentrated sulfuric acid was added to the filtrate under cooling with ice so as to adjust the pH to 4. Precipitated crystals were collected through filtration, washed with water, and dried, to thereby obtain 10.6 g of p-cyanobenzoic acid (yield 72%). The obtained p-cyanobenzoic acid had a purity of 95%.

Example 26

Acetonitrile (20 ml) and p-cyanobenzamide (2.92 g) were placed in a 100-ml three-neck flask disposed in an ice bath. After the solution was cooled, a solution of nitrosonium tetrafluoroborate (2.57 g) in acetonitrile (20 ml) was added dropwise to the solution over five minutes with stirring. When the addition was completed, the solution was further stirred until generation of gas was terminated. The solvent was removed through distillation under reduced pressure, and water (10 ml) was added to the residue. The precipitated crystals were collected through filtration, washed with water, and dried, to thereby obtain 2.77 g of p-cyanobenzoic acid (yield 95%). High performance liquid chromatographic analysis revealed that the p-cyanobenzoic acid obtained had a purity of 99% or more.

Example 27

A 70 wt. % aqueous solution (100 ml) of sulfuric acid and m-cyanobenzamide (2.92 g) were placed in a 200-ml three-neck flask, and the resultant mixture was stirred. Subsequently, a 50 wt. % solution (10 g) of nitrosylsulfuric acid, obtained through dissolution of nitrosylsulfuric acid (5 g) in sulfuric acid (5 g), was added dropwise to the mixture. When the addition was completed, the mixture was allowed to react at room temperature for 30 minutes. The precipitated crystals were collected, washed with water, and dried, to thereby obtain 2.68 g of m-cyanobenzoic acid (yield 92%). The m-cyanobenzoic acid obtained had a purity of 98% or more.

Example 28

Acetic acid (30 ml), acetic anhydride (70 ml), and p-cyanobenzamide (5 g) were mixed with stirring under cooling with ice, to thereby obtain a mixture. The mixture was allowed to react while dinitrogen trioxide gas was introduced thereto at 190 N ml/hour for six hours. The residual solvent was removed through distillation in vacuum, and water was added to the residue, to thereby form crystals. The precipitated crystals were collected through filtration, washed with water, and dried, to thereby obtain 4.73 g of p-cyanobenzoic acid (yield 94%, based on p-cyanobenzamide). High performance liquid chromatographic analysis revealed that the p-cyanobenzoic acid obtained had a purity of 99% or more.

Example 29 m-Cyanobenzamide (2.92 g) was added to a 70 wt. % aqueous sulfuric acid solution (100 ml), and the mixture was stirred under cooling with ice. The mixture was allowed to react while dinitrogen trioxide gas was introduced thereto at 336 N ml/hour for two hours. The precipitated crystals were collected through filtration, washed with water, and dried, to thereby obtain 2.68 g of m-cyanobenzoic acid (yield 92%, based on m-cyanobenzamide). The m-cyanobenzoic acid obtained had a purity of 99% or more.

Example 30

Acetic acid (30 ml), acetic anhydride (70 ml), sodium acetate (6.2 g), and p-cyanobenzamide (5.0 g) were mixed with stirring under cooling with ice, to thereby obtain a mixture. The mixture was allowed to react while dinitrogen tetroxide gas was introduced thereto at 381 N ml/minute for three hours. The residual solvent was removed through distillation in vacuum, and water was added to the residue, to thereby form crystals. The precipitated crystals were collected through filtration, washed with water, and dried, to thereby obtain 4.83 g of p-cyanobenzoic acid (yield 96%, based on p-cyanobenzamide). The p-cyanobenzoic acid obtained had a purity of 97%.

Example 31

Acetic acid (30 ml), acetic anhydride (70 ml), sodium acetate (6.2 g), and m-cyanobenzamide (5.0 g) were mixed with stirring under cooling with ice, to thereby obtain a mixture. The mixture was allowed to react while the mixed gas of nitrogen monoxide and nitrogen dioxide (volume ratio 1:1) was introduced thereto at 286 N ml/minute for four hours. The residual solvent was removed through distillation in vacuum, and water was added to the residue, to thereby form crystals. The precipitated crystals were collected through filtration, washed with water, and dried, to thereby obtain 4.78 g of m-cyanobenzoic acid (yield 94%, based on m-cyanobenzamide). The m-cyanobenzoic acid obtained had a purity of 98%.

Example 32 p-Cyanobenzamide (73.0 g, 0.5 mol) which has a purity of 99% or more and ethanol (460.3 g) were placed in a 2 l-separable flask, and the mixture was allowed to react at 78° C. for 12 hours while a 20% hydrochloric acid/ethanol solution (162.4 g) prepared in advance was added thereto with stirring. Gas chromatographic analysis revealed that the reaction mixture contained 83.1 g of ethyl p-cyanobenzoate (yield 95%). Subsequently, the reaction mixture was concentrated under reduced pressure, and water was added thereto. The resultant mixture was dissolved through heating, and cooled for crystallization, to thereby obtain 74.7 g of ethyl p-cyanobenzoate having a purity of 99.5% (yield 85%).

Example 33 p-Cyanobenzamide (73.0 g, 0.5 mol) which has a purity of 99% or more and methanol (460.3 g) were placed in a 2 l-separable flask, and the mixture was allowed to react at 64° C. for 12 hours while a 20% hydrochloric acid/methanol solution (162.4 g) prepared in advance was added thereto with stirring. Gas chromatographic analysis revealed that the reaction mixture contained 75.7 g of methyl p-cyanobenzoate (yield 94%).

Example 34 p-Cyanobenzamide (73.0 g, 0.5 mol) which has a purity of 99% or more and ethanol (657.0 g) were placed in a 2 l-separable flask, and the mixture was allowed to react at 78° C. for 19 hours while a 95% sulfuric acid (51.6 g) was added thereto with stirring. Gas chromatographic analysis revealed that the reaction mixture contained 66.5 g of ethyl p-cyanobenzoate (yield 76%).

Example 35 m-Cyanobenzamide (73.0 g, 0.5 mol) which has a purity of 99% or more and methanol (460.3 g) were placed in a 2 l-separable flask, and the mixture was allowed to react at 64° C. for 12 hours while a 20% hydrochloric acid/methanol solution (162.4 g) prepared in advance was added thereto with stirring. Gas chromatographic analysis revealed that the reaction mixture contained 74.9 g of methyl p-cyanobenzoate (yield 93%).

Example 36

2,3,5,6-Tetrachloro-4-cyanobenzamide (28.4 g, 0.1 mol) which has a purity of 99% or more and methanol (268.8 g) were placed in a 2 l-separable flask, and the mixture was allowed to react at 64° C. for 12 hours while a 20% hydrochloric acid/methanol solution (91.3 g) prepared in advance was added thereto with stirring. Gas chromatographic analysis revealed that the reaction mixture contained 23.9 g of 2,3,5,6-tetrachloro-4-methyl cyanobenzoate (yield 80%).

Example 37

Terephthalonitrile (12.8 g), 95% sulfuric acid (10.3 g), and ethanol (72.5 g) were placed in a glass autoclave, and the mixture was allowed to react at 130° C. for six hours. The reaction mixture was cooled, and water (9 g) was added thereto. Gas chromatographic analysis revealed that ethyl p-cyanobenzoate had been produced at a yield of 33% and a selectivity of 83%.

Example 38

Terephthalonitrile (12.8 g), hydrogen chloride gas (2.24 NL), and ethanol (72.5 g) were placed in a glass autoclave, and the mixture was allowed to react at 130° C. for six hours. The reaction mixture was cooled, and water (9 g) was added thereto. Gas chromatographic analysis revealed that ethyl p-cyanobenzoate had been produced at a yield of 30% and a selectivity of 96%.

Example 39

Terephthalonitrile (12.8 g), hydrogen chloride gas (2.24 NL), and methanol (72.5 g) were placed in a glass autoclave, and the mixture was allowed to react at 130° C. for seven hours. The reaction mixture was cooled, and water (9 g) was added thereto. Gas chromatographic analysis revealed that methyl p-cyanobenzoate had been produced at a yield of 40% and a selectivity of 91%.

Example 40

Isophthalonitrile (12.8 g), hydrogen chloride gas (2.24 NL), and methanol (72.5 g) were placed in a glass autoclave, and the mixture was allowed to react at 130° C. for seven hours. The reaction mixture was cooled, and water (9 g) was added thereto. Gas chromatographic analysis revealed that methyl m-cyanobenzoate had been produced at a yield of 38% and a selectivity of 83%.

Example 41

Similar procedures as described in Example 37 were performed, and before water was added to the reaction mixture, the terephthalonitrile precipitated was collected through filtration to be used again for reaction, while water was added to the filtrate to obtain ethyl p-cyanobenzoate. Such process was repeated twice. As a result, ethyl p-cyanobenzoate was produced at a yield of 76% based on raw terephthalonitrile (purity 96%).

Example 42

Similar reactions as described in Example 37 were performed, and after the reaction mixture was cooled, water (1.8 g) was added thereto. Subsequently, insoluble terephthalonitrile was collected through filtration to be used again for reaction. This process was repeated twice, and both filtrates were gathered to collect ethyl p-cyanobenzoate, to thereby obtain 12.9 g of ethyl p-cyanobenzoate (purity 94%; yield 75%, based on raw terephthalonitrile).

Example 43

Tetrachloroterephthalonitrile (26.6 g), hydrogen chloride gas (2.24 NL), and methanol (145 g) were placed in a glass autoclave, and the mixture was allowed to react at 140° C. for six hours. The reaction mixture was cooled, and water (18 g) was added thereto. Gas chromatographic analysis revealed that 2,3,5,6-tetrachloro-4-methyl cyanobenzoate had been produced at a yield of 28% and a selectivity of 75%.

Example 44

Terephthalonitrile (64 g, 0.5 mol) and ethanol (850.3 g) were placed in a 2 L four-neck flask, and the resultant mixture was heated to 78° C. with stirring. To the mixture, a 20% aqueous solution (20 g) of sodium hydroxide was added over six hours by use of a tube pump. After the reaction was completed, liquid chromatographic analysis revealed that the reaction mixture contained 48.2 g of p-cyanobenzamide (yield 66%) and 7.4 g of p-cyanobenzoic acid (yield 10%). The reaction mixture was cooled to 30° C., neutralized with concentrated sulfuric acid, and concentrated under reduced pressure so as to remove 508 g of ethanol. After the pressure was restored to normal pressure, the mixture was heated again to 78° C., and a 20% hydrochloric acid/ethanol solution (162.4 g) which was prepared in advance was added to the mixture over six hours by use of a tube pump. The mixture was further stirred for six hours with heat. Gas chromatographic analysis revealed that the reaction mixture contained 65.6 g of ethyl p-cyanobenzoate (yield 75%, based on terephthalonitrile) and diethyl terephthalate (yield 10%, based on terephthalonitrile). After the reaction mixture was cooled to 30° C., the mixture was neutralized with an aqueous solution of sodium hydroxide, and precipitated inorganic salt crystals were collected through filtration. After the filtrate was concentrated and water (350 g) was added thereto, the filtrate was dissolved with heat, and then cooled to 8° C. so as to reprecipitate crystals, to thereby obtain 53.6 g of ethyl p-cyanobenzoate (purity 98.0%) The obtained crude crystals were recrystallized from a solvent of a mixture of water (120 g)/ethanol (120 g), to thereby obtain 46.6 g of ethyl p-cyanobenzoate crystals (purity 99.5%; yield 53%, based on terephthalonitrile).

Example 45

A mixture containing p-cyanobenzylamine (13.2 g), water (50 g), and ferric chloride (0.2 g) was stirred, and a 14 wt. % aqueous solution (200 g) of sodium hypochlorite was added dropwise thereto at room temperature over two hours. The reaction mixture was further stirred for one hour. Subsequently, water (100 g) and urea (4 g) were added to the mixture, and the resultant mixture was further stirred for minutes. The pH of the mixture was adjusted to four through addition of 98 wt. % sulfuric acid. The precipitated crystals were collected through filtration, washed with water, and dried, to thereby obtain 12.1 g of p-cyanobenzoic acid (yield 82%, based on p-cyanobenzylamine). High performance liquid chromatographic analysis revealed that the obtained p-cyanobenzoic acid had a purity of 95%.

Example 46

A mixture containing p-cyanobenzylamine (13.2 g), water (50 g), and ruthenium trichloride (0.2 g) was stirred, and a 14 wt. % aqueous solution (200 g) of sodium hypochlorite was added dropwise thereto at room temperature over two hours. The reaction mixture was further stirred for one hour. Subsequently, water (100 g) and urea (4 g) were added to the mixture, and the resultant mixture was further stirred for 20 minutes. The pH of the mixture was adjusted to four through addition of 98 wt. % sulfuric acid. Precipitated crystals were collected through filtration, washed with water, and dried, to thereby obtain 10.4 g of p-cyanobenzoic acid (yield 76%, based on p-cyanobenzylamine). High performance liquid chromatographic analysis revealed that the p-cyanobenzoic acid obtained had a purity of 95%.

Example 47

A mixture containing p-cyanobenzylamine (13.2 g), dioxane (70 g), sodium carbonate (5.3 g), water (50 g), and ferric nitrate (0.1 g) was stirred, and a 14 wt. % aqueous solution (200 g) of sodium hypochlorite was added dropwise thereto over three hours while inside temperature of a reactor was maintained at 50° C. or lower. The reaction mixture was further stirred for two hours. Subsequently, water (100 g) and urea (4 g) were added to the mixture, and the resultant mixture was further stirred for 20 minutes. The pH of the mixture was adjusted to four through addition of 98 wt. % sulfuric acid. Precipitated crystals were collected through filtration, washed with water, and dried, to thereby obtain 11.9 g of p-cyanobenzoic acid (yield 90%, based on p-cyanobenzylamine). The p-cyanobenzoic acid obtained had a purity of 96%.

Example 48

A mixture containing p-cyanobenzylamine (13.2 g), dioxane (70 g), sodium carbonate (5.3 g), water (50 g), and ruthenium trichloride (0.1 g) was stirred, and a 14 wt. % aqueous solution (200 g) of sodium hypochlorite was added dropwise thereto over three hours while the inside temperature of a reactor was maintained at 50° C. or lower. The reaction mixture was further stirred for two hours. Subsequently, water (100 g) and urea (4 g) were added to the mixture, and the resultant mixture was further stirred for 20 minutes. The pH of the mixture was adjusted to four through addition of 98 wt. % sulfuric acid. Precipitated crystals were collected through filtration, washed with water, and dried, to thereby obtain 13.5 g of p-cyanobenzoic acid (yield 92%, based on p-cyanobenzylamine). The p-cyanobenzoic acid obtained had a purity of 96%.

Example 49

A mixture containing m-cyanobenzylamine (13.2 g), acetonitrile (80 g), sodium hydrogencarbonate (76 g), water (500 g), sodium persulfate (95 g), and iron oxide (0.25 g) was stirred for reaction at 80° C. over ten hours. After the precipitated solid was removed through filtration, the pH of the filtrate was adjusted to 4 through addition of sulfuric acid. The precipitated crystals were collected through filtration, washed with water, dried, to thereby obtain 7.1 g of m-cyanobenzoic acid (yield 48%, based on m-cyanobenzylamine). The m-cyanobenzoic acid obtained had a purity of 94%.

Example 50

A mixture containing m-cyanobenzylamine (13.2 g), acetonitrile (80 g), sodium hydrogencarbonate (76 g), water (500 g), sodium persulfate (95 g), and ruthenium oxide (0.25 g) was stirred for reaction at 80° C. over ten hours. After the precipitated solid was removed through filtration, the pH of the filtrate was adjusted to four through addition of sulfuric acid. The precipitated crystals were collected through filtration, washed with water, and dried, to thereby obtain 8.2 g of m-cyanobenzoic acid (yield 56%, based on m-cyanobenzylamine). The m-cyanobenzoic acid obtained had a purity of 94%.

Example 51

A mixture containing ethyl p-cyanobenzoate (87.5 g, 0.5 mol), methanol (192.5 g), and water (449.2 g) was placed in a 1 l-flask. The mixture was heated to 82° C. with stirring by use of a mechanical stirrer. After the temperature became stable, a 20% aqueous solution of sodium hydroxide was added to the mixture so as to adjust the pH of the mixture at 9.0–9.3. When four hours had elapsed after the reaction started, 20% sodium hydroxide (96.7 g) was added. Liquid chromatographic analysis revealed that the reaction mixture contained 69.1 g of p-cyanobenzoic acid (yield 94%). The reaction mixture was cooled to 30° C., and hydrochloric acid was added to the mixture to lower the pH to 3.1. The mixture was heated again to 82° C., and methanol was added thereto until the mixture dissolved. The resultant mixture was cooled for crystallization, to thereby obtain 64.8 g of p-cyanobenzoic acid crystal (purity 97.5%, yield 86%).

Example 52

A mixture containing ethyl p-cyanobenzoate (87.5 g, 0.5 mol), water (320.8 g), and methanol (320.8 g) was placed in a 1 l-flask. The mixture was heated to 80° C. with stirring by use of a mechanical stirrer. A 20% aqueous solution of sodium hydroxide was added to the mixture so as to adjust the pH of the mixture at 8.0–8.3. Twenty-four hours after the reaction started, liquid chromatographic analysis revealed that the reaction mixture contained 58.9 g of p-cyanobenzoic acid (yield 80.2%). The reaction mixture was cooled to 30° C., and hydrochloric acid was added thereto to lower the pH to 3.1. The mixture was heated again to 82° C. to dissolve. The resultant mixture was cooled for crystallization, to thereby obtain 57.7 g of p-cyanobenzoic acid crystal (purity 96.8%, yield 76%).

Example 53

A mixture containing ethyl p-cyanobenzoate (87.5 g, 0.5 mol), methanol (192.5 g), water (449.2 g) was placed in a 1 l-flask. The mixture was heated to 80° C. with stirring. A 20% aqueous solution of sodium hydroxide was added to the mixture so as to adjust the pH of the mixture at 8.0–8.3. Eighteen hours after the reaction started, liquid chromatographic analysis revealed that the reaction mixture contained 64.7 g of p-cyanobenzoic acid (yield 88%). The reaction mixture was cooled to 30° C., and hydrochloric acid was added thereto to lower the pH to 3.1. The mixture was heated again to 82° C., and methanol was added thereto until the mixture dissolves. The resultant mixture was cooled for crystallization, to thereby obtain 64.6 g of p-cyanobenzoic acid crystal (purity 96.7%, yield 85%).

Example 54

A mixture containing ethyl p-cyanobenzoate (87.5 g, 0.5 mol), ethanol (192.5 g), and water (449.2 g) was placed in a 1 l-flask. The mixture was heated to 82° C. A 20% aqueous solution of sodium hydroxide was added to the mixture so as to adjust the pH of the mixture at 8.0–8.5. Twenty-seven hours after the reaction started, liquid chromatographic analysis revealed that the reaction mixture contained 67.6 g of p-cyanobenzoic acid (yield 92%). The reaction mixture was cooled to 30° C., and hydrochloric acid was added thereto to lower the pH to 3.1. The mixture was heated again to 82° C. to dissolve. The resultant mixture was cooled for crystallization, to thereby obtain 64.2 g of p-cyanobenzoic acid crystal (purity 95.0%, yield 83%).

Example 55

A mixture containing ethyl p-cyanobenzoate (87.5 g, 0.5 mol), methanol (192.5 g), and water (449.2 g) was placed in a 1 l-flask. The mixture was heated to 82° C., and triethylamine was added thereto so as to adjust the pH of the mixture at 9.0–9.3. Six hours after the reaction started, liquid chromatographic analysis revealed that the reaction mixture contained 67.6 g of p-cyanobenzoic acid (yield 92%). The reaction mixture was cooled to 30° C., and hydrochloric acid was added thereto to lower the pH to 3.1. The mixture was heated again to 82° C., and methanol was added thereto so that the mixture dissolves. The resultant mixture was cooled for crystallization, to thereby obtain 62.4 g of p-cyanobenzoic acid crystal (purity 97.8%, yield 83%).

Example 56

A mixture containing ethyl p-cyanobenzoate (87.5 g, 0.5 mol), ethanol (192.5 g), and water (449.2 g) was placed in a 1 l-flask. The mixture was heated to 82° C., and sodium hydrogencarbonate was added thereto so as to adjust the pH of the mixture at 9.0–9.3. Seven hours after the reaction started, liquid chromatographic analysis revealed that the reaction mixture contained 67.6 g of p-cyanobenzoic acid (yield 92%).

Example 57

A mixture containing ethyl p-cyanobenzoate (87.5 g, 0.5 mol), ethanol (192.5 g), and water (449.2 g) was placed in a 1 l-flask. The mixture was heated to 60° C., and a 20% aqueous solution of sodium hydroxide was added thereto so as to adjust the pH of the mixture at 9.9–10.0. Twenty-three hours after the reaction started, liquid chromatographic analysis revealed that the reaction mixture contained 60.3 g of p-cyanobenzoic acid (yield 82%).

Example 58

A mixture containing ethyl m-cyanobenzoate (87.5 g, 0.5 mol), methanol (192.5 g), and water (449.2 g) was placed in a 1 l-flask, and heated to 82° C. with stirring by use of a mechanical stirrer. When the temperature became stable, a 20% aqueous solution of sodium hydroxide was added thereto so as to adjust the pH of the mixture at 9.0–9.3. Four hours after the reaction started, 20% sodium hydroxide (98.2 g) was added to the mixture. Liquid chromatographic analysis revealed that the reaction mixture contained 68.4 g of m-cyanobenzoic acid (yield 93%). The reaction mixture was cooled to 30° C., and hydrochloric acid was added thereto to lower the pH of the mixture to 3.1. The mixture was heated again to 82° C., and methanol was added thereto until the mixture dissolves. The mixture was cooled so as to crystallize, to thereby obtain 63.8 g of m-cyanobenzoic acid crystal (purity 96.8%, yield 84%).

Example 59

A mixture containing 2,3,5,6-tetrachloro-4-methyl cyanobenzoate (29.9 g, 0.1 mol), methanol (149.5 g), and water (234.3 g) was placed in a 1 l-flask, and heated to 70° C. with stirring by use of a mechanical stirrer. When the temperature became stable, a 20% aqueous solution of sodium hydroxide (20 g) was added thereto over two hours so as to adjust the pH of the mixture at 8.0–8.2. Liquid chromatographic analysis revealed that the reaction mixture contained 26.2 g of 2,3,5,6-tetrachloro-4-cyanobenzoic acid (yield 92%). The reaction mixture was cooled, and hydrochloric acid was added thereto to lower the pH of the mixture to three. The precipitated crystals were collected through filtration, to thereby obtain 23.8 g of 2,3,5,6-tetrachloro-4-cyanobenzoic acid (purity 96%, yield 80%).

Example 60

A mixture containing p-cyanobenzoyl chloride (16.6 g), p-cyanobenzoic acid (14.7 g), and dimethylformamide (0.15 g) was stirred vigorously at 120° C., and phosgene gas (20 g) was introduced into the mixture over 90 minutes. After dry nitrogen gas was introduced into the reaction mixture for one hour, the mixture was distilled under reduced pressure, to thereby obtain 32.5 g of p-cyanobenzoyl chloride (yield 98%, based on p-cyanobenzoic acid; bp. 110° C./2 mmHg). Gas chromatographic analysis revealed that the obtained p-cyanobenzoyl chloride had a purity of 99% or more.

Example 61

A mixture containing p-cyanobenzoyl chloride (16.6 g), p-cyanobenzoic acid (14.7 g), imidazole (0.2 g), and xylene (150 ml) was stirred vigorously at 140° C., and phosgene gas (20 g) was introduced to the mixture over two hours. After dry nitrogen gas was introduced to the reaction mixture for one hour, the mixture was distilled under reduced pressure, to thereby obtain 31.8 g of p-cyanobenzoyl chloride (yield 96%, based on p-cyanobenzoic acid). The p-cyanobenzoyl chloride obtained had a purity of 99% or more.

Example 62 p-Cyanobenzoic acid (14.7 g) and acetonitrile (300 ml) were mixed and stirred vigorously while the solvent was refluxed, and phosgene gas (30 g) was introduced to the mixture over four hours. After dry nitrogen gas was introduced to the reaction mixture for one hour, acetonitrile was removed under ambient pressure, and was further removed under reduced pressure through distillation, to thereby obtain 16.2 g of p-cyanobenzoyl chloride (yield 98%, based on p-cyanobenzoic acid). The p-cyanobenzoyl chloride obtained had a purity of 99%.

Example 63

A mixture containing m-cyanobenzoyl chloride (16.6 g) and m-cyanobenzoic acid (14.7 g) was stirred vigorously at 130° C., and phosgene gas (20 g) was introduced to the mixture over two hours. After dry nitrogen gas was introduced to the reaction mixture for one hour, the mixture was distilled under reduced pressure, to thereby obtain 31.8 g of m-cyanobenzoyl chloride (yield 96%, based on m-cyanobenzoicacid; bp. 127° C./11 mmHg). The p-cyanobenzoyl chloride obtained had a purity of 99% or more.

Example 64

A mixture containing pyridine (8.7 g) and dichloromethane (150 ml) was stirred vigorously at room temperature. A solvent wherein phosgene (10.4 g) was dissolved in dichloromethane (150 ml) was added to the mixture, and stirred. p-cyanobenzoic acid (14.7 g) was added to the reaction mixture, and stirred vigorously at room temperature for one hour. Gas chromatographic analysis revealed that the p-cyanobenzoyl chloride obtained had been produced at a yield of 98% and had a purity of 99% or more.

Example 65

A mixture containing m-cyanobenzoic acid (14.7 g), a phosgene trimer (14.8 g), pyridine (11.9 g), and 1,2-dichloroethane (300 ml) was stirred vigorously at 90° C. for four hours. The reaction mixture was cooled, and gas chromatographic analysis revealed that the m-cyanobenzoyl chloride obtained had been produced at a yield of 99% based on m-cyanobenzoic acid and had a purity of 99% or more.

As described hereinabove, the present invention provides a process for producing a cyanobenzamide compound with high selectivity and yield, which process comprises hydrolyzing one nitrile group of an easily available phthalonitrile compound.

The invention also provides a process for producing a cyanobenzoic acid compound and a cyanobenzoate ester compound without affecting the cyano group of the benzene ring, which process comprises transforming, under acidic conditions, the thus-produced cyanobenzamide compound serving as a starting material into the target compounds.

The invention also provides a process for producing an alkyl cyanobenzoate compound with high selectivity and yield, which process comprises reacting a phthalonitrile compound serving as a starting material with an aliphatic alcohol in the presence of an acid, to thereby selectively transform one nitrile group into an imino ether group.

The invention also provides a process for producing a cyanobenzoic acid compound without affecting the cyano group of the benzene ring, which process comprises oxidizing a cyanobenzylamine compound serving as a starting material.

The invention also provides a process for producing a cyanobenzoic acid compound with high selectivity and yield without affecting the cyano group of the benzene ring, which process comprises hydrolyzing an alkyl cyanobenzoate compound.

The invention also provides a process for producing a cyanobenzoyl chloride compound without affecting the cyano group of the benzene ring, which process comprises chlorinating a cyanobenzoic acid compound serving as a starting material.

The cyanobenzoic acid compound, cyanobenzamide compound, alkyl cyanobenzoate compound, and cyanobenzoyl chloride compound produced through the process according to the present invention are useful intermediates for a variety of chemicals such as pharmaceuticals, agrochemicals, liquid crystals, and monomers for functional polymers.

While the invention has been described in detail and with reference to specific embodiments thereof, it will be apparent to one skilled in the art that various changes and modifications can be made therein without departing from the spirit and scope thereof.

What is claimed is:

1. A process for producing a cyanobenzoic acid compound, which comprises employing either (i) hypohalogenous acid and/or halogenous acid, (ii) nitrate salt, (iii) nitrosonium salt, or (iv) nitrogen oxide to transform a cyanobenzamide compound into a cyanobenzoic acid compound under an acidic condition.

2. A process for producing a cyanobenzoic acid compound according to claim 1, wherein the process comprises reacting the cyanobenzamide compound with hypohalogenous acid and/or halogenous acid under an acidic condition to thereby exclusively transform the amide group into a carboxyl group.

3. A process for producing a cyanobenzoic acid compound according to claim 1, wherein the process comprises selectively hydrating one nitrile group of a phthalonitrile compound in an aliphatic alcohol serving as a solvent in the presence of a base to thereby produce a cyanobenzamide compound, and reacting the cyanobenzamide compound with hypohalogenenous acid and/or halogenous acid under an acidic condition to thereby exclusively transform the amide group into a carboxyl group.

4. A process for producing a cyanobenzoic acid compound according to claim 1, wherein the process comprises reacting the cyanobenzamide compound with hypohalogenenous acid and/or halogenous acid under an acidic condition with the reaction mixture having a pH of 7 or less.

5. A process for producing a cyanobenzoic acid compound according to claim 1, wherein the process comprises reacting the cyanobenzamide compound with nitrous acid under an acidic condition.

6. A process for producing a cyanobenzoic acid compound according to claim 5, wherein the process includes generating nitrous acid from a nitrite salt and an acid.

7. A process for producing a cyanobenzoic acid compound according to claim 5, wherein the reacting is carried out in a strongly acidic aqueous solvent at 5–60° C.

8. A process for producing a cyanobenzoic acid compound according to claim 5, wherein the reacting is carried out in a substantially water-free and acidic organic solvent in the temperature range of −10° C. to 100° C.

9. A process for producing a cyanobenzoic acid compound according to claim 5, wherein the process comprises reacting 1 mol of a cyanobenzamide compound with a nitrite salt in an amount at least equimol to 10 mol.

10. A process for producing a cyanobenzoic acid compound according to claim 1, wherein the process comprises reacting the cyanobenzamide compound with a nitrosonium salt compound under an acidic condition.

11. A process for producing a cyanobenzoic acid compound according to claim 10, wherein the reacting is carried out in a substantially water-free organic solvent.

12. A process for producing a cyanobenzoic acid compound according to claim 1, wherein the process comprises reacting the cyanobenzamide compound with a nitrogen oxide.

13. A process for producing a cyanobenzoic acid compound according to claim 12, wherein the reacting is carried out in an organic solvent.

14. A process for producing a cyanobenzoic acid compound according to claim 13, wherein the organic solvent is a polar organic solvent.

15. A process for producing a cyanobenzoic acid compound according to claim 14, wherein the polar organic solvent is a mixture of a carboxylic acid and a carboxylic anhydride.

16. A process for producing a cyanobenzoic acid compound according to claim 12, wherein, the reacting is carried out in the presence of a base.

17. A process for producing a cyanobenzoic acid compound according to claim 16, wherein the base is a carboxylate salt.

18. A process for producing a cyanobenzoic acid compound according to claim 12, wherein the reacting is carried out in an aqueous acidic solution.

19. A process for producing a cyanobenzoic acid compound according to claim 1, wherein the cyanobenzamide compound is a compound represented by the following formula:

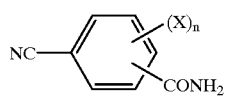

(1)

wherein each of —CONH$_2$ and —X represents a substituent of the benzene ring; the —CONH$_2$ group is bonded at the m- or the p-position with respect to the CN group; X represents a chlorine atom or a fluorine atom; n is an integer between 0 and 4 inclusive; and when n is 2 or more the plurality of X's may be identical to or different from one another, and the cyanobenzoic acid compound is a compound represented by the following formula:

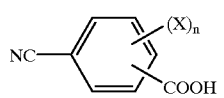

(2)

wherein each of —COOH and —X represents a substituent of the benzene ring; the —COOH group is bonded at the m- or the p-position with respect to the CN group; X represents a chlorine atom or a fluorine atom; n is an integer between 0 and 4 inclusive; and when n is 2 or more the plurality of X's may be identical to or different from one another.

20. A process for producing a cyanobenzoic acid compound according to claim 19, wherein the cyanobenzamide compound represented by formula (1) is m-cyanobenzamide or p-cyanobenzamide, and the cyanobenzoic acid compound represented by formula (2) is m-cyanobenzoic acid or p-cyanobenzoic acid.

21. A process for producing a cyanobenzamide compound, which comprises selectively hydrating one nitrile group of a phthalonitrile compound in an aliphatic alcohol serving as a solvent, in the presence of a base, wherein the base is present in an amount of from 0.01–1 mol based on 1 mol of phthalonitrile compound, and the base comprises one or more bases selected from the group consisting of an alkali metal hydroxide, an alkali metal carbonate, an alkali metal phosphate, an alkaline earth metal hydroxide, and an amine.

22. A process for producing a cyanobenzamide compound according to claim 21, wherein the phthalonitrile compound is a compound represented by the following formula:

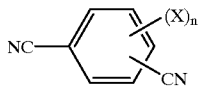 (3)

wherein one nitrile group is bonded at the m- or the p-position with respect to the other nitrile group; X represents a chlorine atom or a fluorine atom; n is an integer between 0 and 4 inclusive; and when n is 2 or more the plurality of X's may be identical to or different from one another, and the cyanobenzamide compound is a compound represented by the following formula:

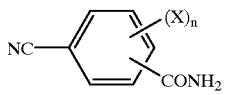 (1)

wherein X and n have the same definitions as described above, and the —CONH$_2$ group is bonded at the m- or the p-position with respect to the CN group.

23. A process for producing a cyanobenzamide compound according to claim 22, wherein the phthalonitrile compound represented by formula (3) is isophthalonitrile or terephthalonitrile, and the cyanobenzamide compound represented by formula (1) is m- or p-cyanobenzamide.

24. A process for producing a cyanobenzamide compound according to claim 21, wherein the aliphatic alcohol is a tertiary alcohol.

25. A process for producing a cyanobenzamide compound according to claim 21, wherein the hydrating is carried out within the temperature range of 0° C. to the reflux temperature of the employed solvent.

26. A process for producing a cyanobenzamide compound according to claim 21, wherein during the hydrating water is added in an amount of 0.2–10 mol based on 1 mol of the phthalonitrile compound.

27. A process for producing an alkyl cyanobenzoate compound from a phthalonitrile compound, which comprises reacting a phthalonitrile compound and an aliphatic alcohol in the presence of an acid to thereby transform exclusively one nitrile group into an alkylimino ether group; and selectively reacting the formed alkylimino ether group with water to thereby transform the ether group into an alkyl ester group.

28. A process for producing an alkyl cyanobenzoate compound from a phthalonitrile compound according to claim 27, wherein the phthalonitrile compound is a compound represented by the following formula:

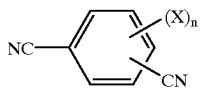 (3)

wherein each of —CN and X represents a substituent of the benzene ring; one nitrile group is bonded at the m- or the p-position with respect to the other nitrile group; X represents a chlorine atom or a fluorine atom; n is an integer between 0 and 4 inclusive; and when n is 2 or more the plurality of X's may be identical to or different from one another, the aliphatic alcohol in the first step is represented by the following formula

 ROH (4)

wherein R represents a C$_1$–C$_5$ alkyl group,
and the alkyl cyanobenzoate compound is a compound represented by the following formula:

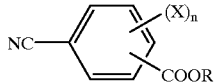 (5)

wherein X, n, and R have the same definitions as described above and the —COOR group is bonded at the m- or the p-position with respect to the nitrile group.

29. A process for producing an alkyl cyanobenzoate compound from a phthalonitrile compound according to claim 27, wherein the phthalonitrile compound represented by formula (3) is isophthalonitrile or terephthalonitrile, and the alkyl cyanobenzoate compound represented by formula (5) is alkyl m- or p-cyanobenzoate.

30. A process for producing an alkyl cyanobenzoate compound from a phthalonitrile compound according to claim 27, wherein the aliphatic alcohol represented by formula (4) is methanol or ethanol.

31. A process for producing an alkyl cyanobenzoate compound from a phthalonitrile compound according to claim 27, wherein the unreacted phthalonitrile compound is collected and reused as a raw material.

32. A process for producing an alkyl cyanobenzoate compound, which comprises reacting a cyanobenzamide compound and an aliphatic alcohol in the presence of an acid to thereby transform exclusively the amide group into an alkyl ester group.

33. A process for producing an alkyl cyanobenzoate compound according to claim 34, wherein the cyanobenzamide compound is a compound represented by the following formula:

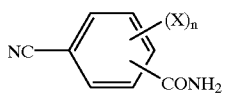 (1)

wherein each of —CONH$_2$ and —X represents a substituent of the benzene ring; the —CONH$_2$ group is bonded at the m- or the p-position with respect to the CN group; X represents a chlorine atom or a fluorine atom; n is an integer between 0 and 4 inclusive; and when n is 2 or more the plurality of X's may be identical to or different from one another, the aliphatic alcohol is represented by the following formula:

ROH  (4)

wherein R represents a $C_1$–$C_5$ alkyl group, and the alkyl cyanobenzoate compound is represented by the following formula:

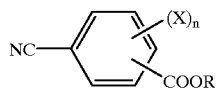  (5)

wherein X, n, and R have the same definitions as described above and the —COOR group is bonded at the m- or the p-position with respect to the nitrile group.

34. A process for producing an alkyl cyanobenzoate compound according to claim 33, wherein the cyanobenzamide compound represented by formula (1) is m- or p-cyanobenzamide, and the alkyl cyanobenzoate compound represented by formula (5) is alkyl m- or p-cyanobenzoate.

35. A process for producing an alkyl cyanobenzoate compound according to claim 34, wherein the aliphatic alcohol represented by formula (4) is methanol or ethanol.

36. A process for producing a cyanobenzoic acid compound, which comprises oxidizing a cyanobenzylamine compound.

37. A process for producing a cyanobenzoic acid compound according to claim 36, wherein the process comprises oxidizing the cyanobenzylamine compound oxidized in the presence of a ruthenium oxide compound or an iron oxide compound.

38. A process for producing a cyanobenzoic acid compound according to claim 36, wherein the oxidizing is carried out by use of an oxidizing agent other than a ruthenium oxide compound or an iron oxide compound, in the presence of the ruthenium oxide compound or the iron oxide compound.

39. A process for producing a cyanobenzoic acid compound according to claim 38, wherein the oxidizing agent is a hypohalogeous acid compound or a persulfate salt compound.

40. A process for producing a cyanobenzoic acid compound according to claim 36, wherein the oxidizing is carried out in water or water containing an aprotic polar solvent.

41. A process for producing a cyanobenzoic acid compound according to claim 36, wherein the oxidizing is carried out at a pH of 7.5–12.

42. A process for producing a cyanobenzoic acid compound according to claim 36, wherein the cyanobenzylamine compound is a compound represented by the following formula:

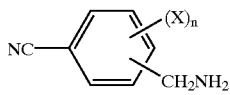  (6)

wherein each of —$CH_2NH_2$ and —X represents a substituent of the benzene ring; the —$CH_2NH_2$ group is bonded at the m- or the p-position with respect to the CN group; X represents a chlorine atom or a fluorine atom; n is an integer between 0 and 4 inclusive; and when n is 2 or more the plurality of X's may be identical to or different from one another, and the cyanobenzoic acid compound is a compound represented by the following formula:

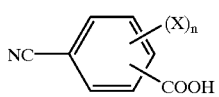  (2)

wherein each of —COOH and —X represents a substituent of the benzene ring; the —COOH group is bonded at the m- or p-position with respect to the —CN group; —X represents a chlorine atom or a fluorine atom; n is an integer between 0 and 4 inclusive; and when n is 2 or more the plurality of X's may be identical to or different from one another.

43. A process for producing a cyanobenzoic acid compound according to claim 42, wherein the cyanobenzylamine compound represented by formula (6) is m- or p-cyanobenzylamine, and the cyanobenzoic acid compound represented by formula (2) is m- or p-cyanobenzoic acid.

44. A process for producing a cyanobenzoic acid compound represented by the following formula:

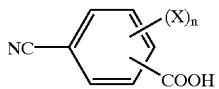  (2)

wherein each of —COOH and —X represents a substituent of the benzene ring; the —COOH group is bonded at the m- or the p-position with respect to the CN group; X represents a chlorine atom or a fluorine atom; n is 2 or more the plurality of X's may be identical to or different from one another, which process comprises (1) exclusively hydrolyzing the alkyl ester group of an alkyl cyanobenzoate compound represented by the following formula:

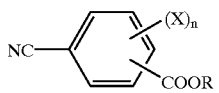  (5)

wherein each of —COOR and —X represents a substituent of the benzene ring; X represents a chlorine atom or a fluorine atom; n is an integer between 0 and 4 inclusive; and when n is 2 or more the plurality of X's may be identical to or different from one another; R represents a $C_1$–$C_5$ alkyl group; and the —COOR group is bonded at the m- or the p-position with respect to the nitrile group, in the presence of a base, to thereby synthesize a salt of the corresponding cyanobenzoic acid compound, and (2) adding an acid in order to release the corresponding free cyanobenzoic acid compound.

45. A process for producing a cyanobenzoic acid compound according to claim 44, wherein the alkyl cyanobenzoate compound represented by formula (5) is alkyl m-cyanobenzoate or alkyl p-cyanobenzoate, and the cyanobenzoic acid compound represented by formula (2) is m-cyanobenzoic acid or p-cyanobenzoic acid.

46. A process for producing a cyanobenzoic acid compound according to claim 44, wherein the hydrolyzing is carried out in the presence of an alkali metal hydroxide or carbonate in (1).

47. A process for producing a cyanobenzoic acid compound according to claim 44, wherein the hydrolyzing is carried out at a pH of 8–12 in (1).

48. A process for producing a cyanobenzoic acid compound according to claim 44, wherein the alkyl cyanobenzoate compound represented by formula (5) is methyl cyanobenzoate or ethyl cyanobenzoate.

* * * * *